United States Patent
Schabbach et al.

(10) Patent No.: US 12,332,104 B2
(45) Date of Patent: Jun. 17, 2025

(54) SENSOR, CARTRIDGE AND DRUG DELIVERY DEVICE

(71) Applicant: Sanofi-Aventis Deutschland GMBH, Frankfurt am Main (DE)

(72) Inventors: Michael Schabbach, Frankfurt am Main (DE); Christian Nessel, Frankfurt am Main (DE); Daniel Auernhammer, Frankfurt am Main (DE); Beate Franke, Frankfurt am Main (DE); Francisco Soares, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 18/475,417

(22) Filed: Sep. 27, 2023

(65) Prior Publication Data
US 2024/0019289 A1  Jan. 18, 2024

Related U.S. Application Data

(63) Continuation of application No. 17/116,477, filed on Dec. 9, 2020, now Pat. No. 11,802,787, which is a
(Continued)

(30) Foreign Application Priority Data

Jul. 31, 2015 (EP) .................................... 15179216

(51) Int. Cl.
*G01F 23/263* (2022.01)
*A61M 5/31* (2006.01)
(Continued)

(52) U.S. Cl.
CPC ....... *G01F 23/268* (2013.01); *A61M 5/31568* (2013.01); *G01F 23/2845* (2013.01);
(Continued)

(58) Field of Classification Search
CPC .... G01F 23/268; G01F 23/00; G01F 23/2845; G01F 23/2921; G01F 23/2925;
(Continued)

(56) References Cited

U.S. PATENT DOCUMENTS 4,785,672 A * 11/1988 Picone .................... G01F 1/584
73/861.14
4,984,462 A 1/1991 Hass, Jr. et al.
(Continued)

FOREIGN PATENT DOCUMENTS

CN    1545681       11/2004
CN    101405582     4/2009
(Continued)

OTHER PUBLICATIONS

PCT International Preliminary Report on Patentability in International Application No. PCT/EP2016/067811, dated Feb. 6, 2018, 8 pages.
(Continued)

*Primary Examiner* — Paul M. West
(74) *Attorney, Agent, or Firm* — Bond, Schoeneck & King, PLLC

(57) ABSTRACT

In one aspect the present disclosure relates to a sensor for measuring at least one physical or chemical parameter of a cartridge or syringe filled with a liquid substance. In further aspects the disclosure relates to a cartridge equipped with such a sensor as well as to a drug delivery device equipped with such a cartridge, wherein the sensor comprises:
a planar flexible foil arrangeable to an outer circumference of a barrel of the cartridge or syringe,
at least a first and a second measuring electrode arranged on said foil, and at least a first and a second contact electrode arranged on said foil,
(Continued)

wherein the first contact electrode is connected to the first measuring electrode and wherein the second contact electrode is connected to the second measuring electrode.

20 Claims, 9 Drawing Sheets

Related U.S. Application Data continuation of application No. 15/748,309, filed as application No. PCT/EP2016/067815 on Jul. 26, 2016, now Pat. No. 10,895,487.

(51) Int. Cl.
| | |
|---|---|
| A61M 5/315 | (2006.01) |
| G01F 23/00 | (2022.01) |
| G01F 23/284 | (2006.01) |
| G01F 23/292 | (2006.01) |
| A61M 5/168 | (2006.01) |
| A61M 5/20 | (2006.01) |
| A61M 5/24 | (2006.01) |
| G01N 21/59 | (2006.01) |

(52) U.S. Cl.
CPC ...... *G01F 23/2921* (2013.01); *G01F 23/2925* (2013.01); *G01F 23/2927* (2013.01); *A61M 5/1684* (2013.01); *A61M 5/20* (2013.01); *A61M 5/2459* (2013.01); *A61M 2005/3126* (2013.01); *A61M 5/3155* (2013.01); *A61M 2205/3317* (2013.01); *A61M 2205/3368* (2013.01); *A61M 2205/3389* (2013.01); *A61M 2205/3584* (2013.01); *A61M 2205/3673* (2013.01); *A61M 2205/50* (2013.01); *A61M 2205/52* (2013.01); *A61M 2205/583* (2013.01); *A61M 2205/70* (2013.01); *A61M 2205/8206* (2013.01); *A61M 2205/8212* (2013.01); *A61M 2205/8243* (2013.01); *A61M 2205/8293* (2013.01); *G01F 23/00* (2013.01); *G01N 21/59* (2013.01)

(58) Field of Classification Search
CPC ....... G01F 23/2927; A61M 2205/3126; A61M 2205/3368; A61M 2205/50; A61M 2205/52; A61M 2205/583; A61M 2205/70; A61M 2205/8206; A61M 5/31568
See application file for complete search history.

(56) References Cited

U.S. PATENT DOCUMENTS

| | | | |
|---|---|---|---|
| 6,110,148 | A | 8/2000 | Brown et al. |
| 6,830,558 | B2 | 12/2004 | Flaherty et al. |
| 9,186,465 | B2 | 11/2015 | Jorgensen et al. |
| 9,486,586 | B2 | 11/2016 | Jugl et al. |
| 9,849,252 | B2 | 12/2017 | Armes |
| 10,895,487 | B2 | 1/2021 | Schabbach et al. |
| 10,898,647 | B2 | 1/2021 | Schabbach et al. |
| 11,007,322 | B2 | 5/2021 | Schabbach et al. |
| 11,020,529 | B2 | 6/2021 | Scabbach et al. |
| 11,596,744 | B2 | 3/2023 | Schabbach et al. |
| 2001/0037680 | A1 | 11/2001 | Buck et al. |
| 2002/0188259 | A1 | 12/2002 | Hickle et al. |
| 2003/0034785 | A1 | 2/2003 | Palata |
| 2004/0025877 | A1 | 2/2004 | Crowder et al. |
| 2005/0154345 | A1 | 7/2005 | Milleker et al. |
| 2007/0270744 | A1 | 11/2007 | Dacquay et al. |
| 2008/0124085 | A1* | 5/2008 | Yoshikawa ............ G08C 23/04 398/106 |
| 2009/0069756 | A1 | 3/2009 | Larsen |
| 2009/0318876 | A1 | 12/2009 | Hansen et al. |
| 2010/0102799 | A1 | 4/2010 | Schnidrig |
| 2010/0286654 | A1 | 11/2010 | Dos Santos et al. |
| 2011/0004188 | A1 | 1/2011 | Shekalim |
| 2011/0009824 | A1 | 1/2011 | Yodfat et al. |
| 2011/0270188 | A1 | 11/2011 | Caffey et al. |
| 2012/0165759 | A1* | 6/2012 | Rogers ................. A61B 5/6867 606/228 |
| 2013/0150689 | A1 | 6/2013 | Shaw-Klein |
| 2013/0222135 | A1* | 8/2013 | Stein ..................... A61J 7/0418 222/23 |
| 2014/0076766 | A1 | 3/2014 | Key |
| 2014/0296823 | A1 | 10/2014 | Ward et al. |
| 2015/0122015 | A1 | 5/2015 | Leppard |
| 2015/0126963 | A1 | 5/2015 | Despa et al. |
| 2015/0268656 | A1 | 9/2015 | Bammer et al. |
| 2016/0151558 | A1 | 6/2016 | Tobescu |
| 2017/0011970 | A1 | 1/2017 | Cheng et al. |
| 2017/0119970 | A1 | 5/2017 | Bammer et al. |
| 2017/0119971 | A1 | 5/2017 | Marsh et al. |
| 2018/0224315 | A1 | 8/2018 | Schabbach et al. |
| 2018/0228977 | A1 | 8/2018 | Schabbach et al. |
| 2018/0236172 | A1 | 8/2018 | Schabbach et al. |
| 2019/0022322 | A1 | 1/2019 | Schabbach et al. |
| 2021/0116287 | A1 | 4/2021 | Schabbach et al. |
| 2021/0236734 | A1 | 8/2021 | Schabbach et al. |

FOREIGN PATENT DOCUMENTS

| | | |
|---|---|---|
| CN | 101405749 | 4/2009 |
| CN | 101484783 | 7/2009 |
| CN | 102019011 | 4/2011 |
| CN | 104582765 | 4/2015 |
| CN | 104740714 | 7/2015 |
| CN | 104812424 | 7/2015 |
| DE | 3329689 | 3/1984 |
| EP | 2182456 | 5/2010 |
| EP | 2284849 A1 | 2/2011 |
| EP | 2982400 | 2/2016 |
| JP | S58-149878 | 9/1983 |
| JP | S59-034117 | 4/1985 |
| JP | S60-059120 | 4/1985 |
| JP | 2005-514965 | 5/2005 |
| JP | 2009-522031 | 6/2009 |
| JP | 2009-542388 | 12/2009 |
| JP | 2012-507314 | 3/2012 |
| JP | 2013-506444 | 3/2015 |
| JP | 2015-511836 | 4/2015 |
| JP | 2015-532136 | 11/2015 |
| WO | WO 2006/021295 | 3/2006 |
| WO | WO 2007/077224 | 7/2007 |
| WO | WO 2007/107558 | 9/2007 |
| WO | WO 2007/107562 | 9/2007 |
| WO | WO 2008/003625 | 1/2008 |
| WO | WO 2010/052275 | 5/2010 |
| WO | WO 2011/039205 | 4/2011 |
| WO | WO 2013/050535 | 4/2013 |
| WO | WO 2013/120775 | 8/2013 |
| WO | WO 2014/052997 | 4/2014 |
| WO | WO 2014/118111 | 8/2014 |
| WO | WO 2014/139914 | 9/2014 |

OTHER PUBLICATIONS

PCT International Preliminary Report on Patentability in International Application No. PCT/EP2016/067813, dated Feb. 6, 2018, 8 pages.
PCT International Preliminary Report on Patentability in International Application No. PCT/EP2016/067814, dated Feb. 6, 2018, 8 pages.
PCT International Preliminary Report on Patentability in International Application No. PCT/EP2016/067815, dated Feb. 6, 2018, 10 pages.
PCT International Search Report and Written Opinion in International Application No. PCT/EP2016/067811, dated Nov. 3, 2016, 11 pages.

(56) References Cited

OTHER PUBLICATIONS

PCT International Search Report and Written Opinion in International Application No. PCT/EP2016/067813, dated Nov. 3, 2016, 11 pages.
PCT International Search Report and Written Opinion in International Application No. PCT/EP2016/067814, dated Nov. 2, 2016, 11 pages.
PCT International Search Report and Written Opinion in International Application No. PCT/EP2016/067815, dated Nov. 3, 2016, 12 pages.
English translation of DE3329689. (Year: 1984).
U.S. Appl. No. 15/748,756, filed Jan. 30, 2018, Michael Schabbach.
U.S. Appl. No. 17/230,165, filed Apr. 14, 2021, Michael Schabbach.
U.S. Appl. No. 15/748,898, filed Jan. 30, 2018, Michael Schabbach.
U.S. Appl. No. 15/748,217, filed Jan. 29, 2018, Michael Schabbach.

* cited by examiner

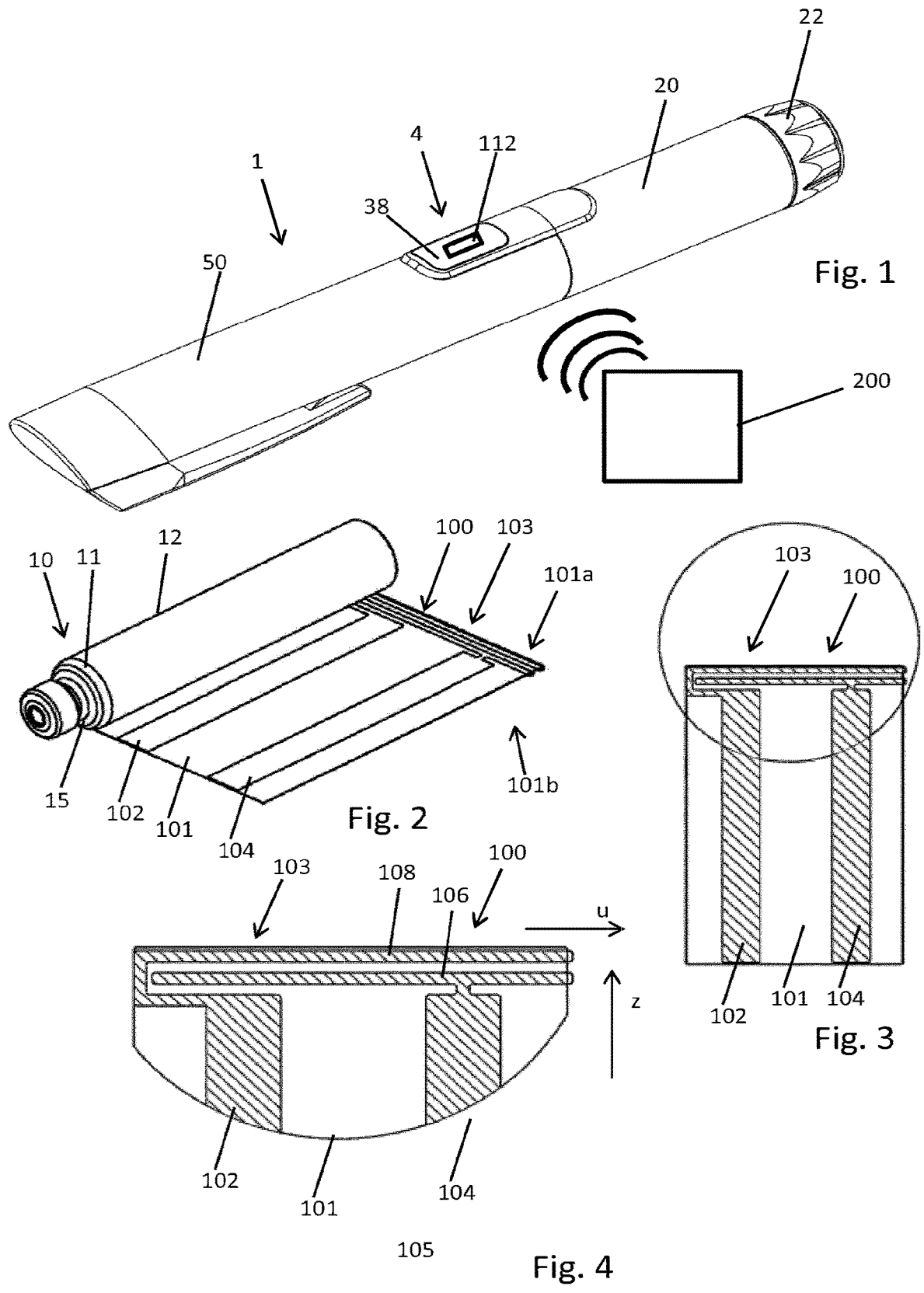

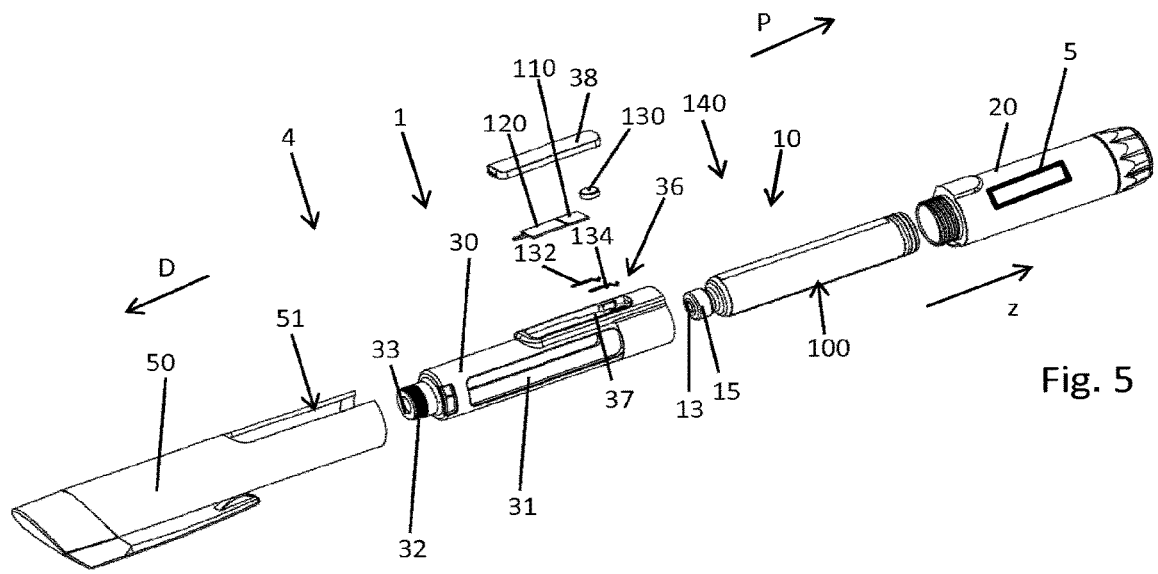
Fig. 5
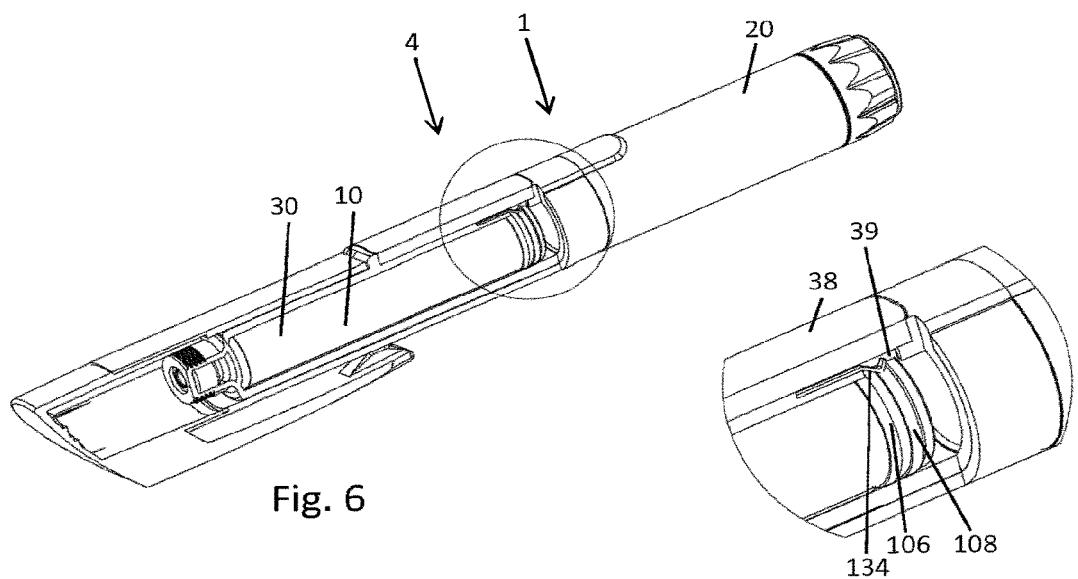
Fig. 6
Fig. 7

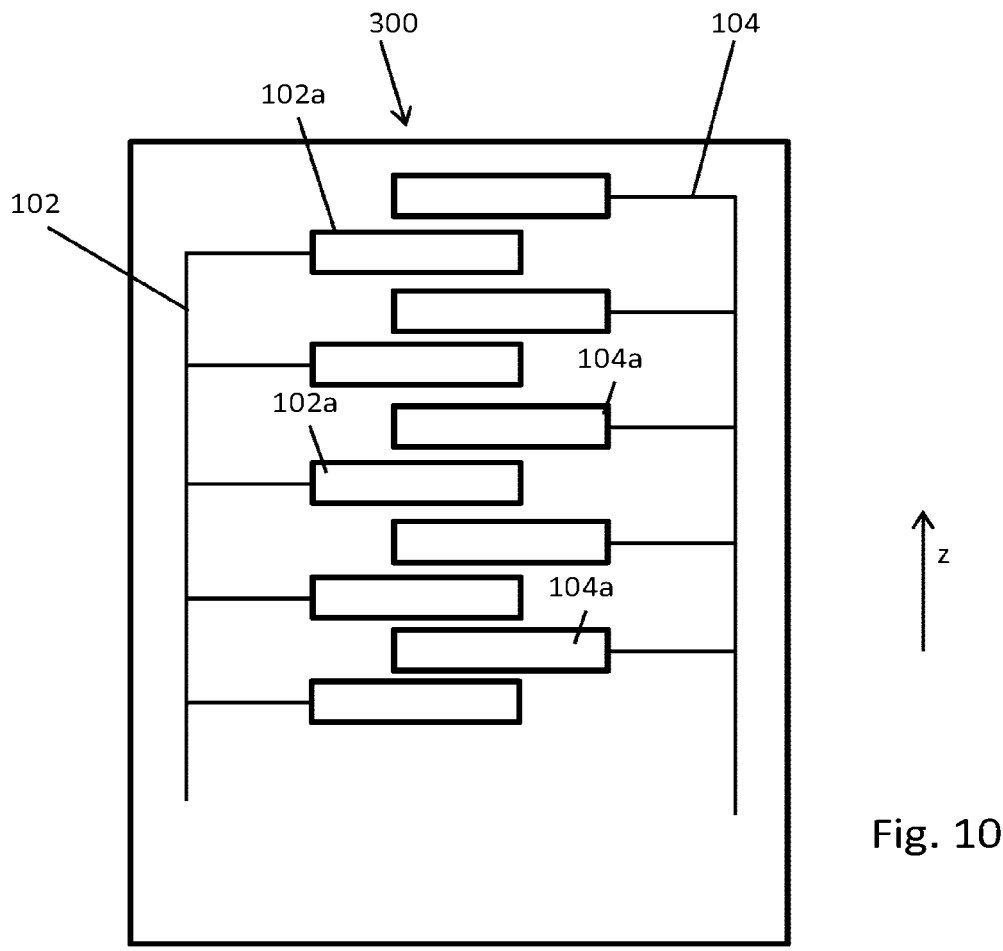
Fig. 10
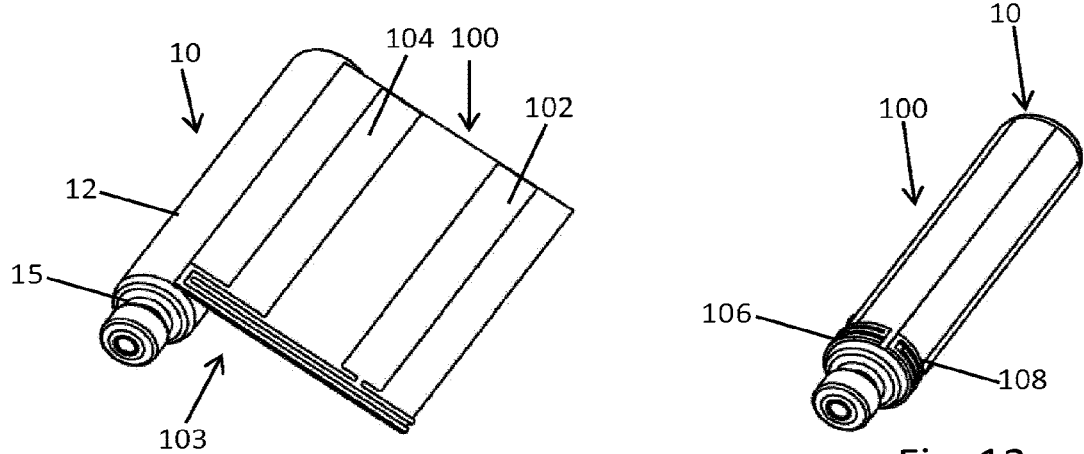
Fig. 11
Fig. 12

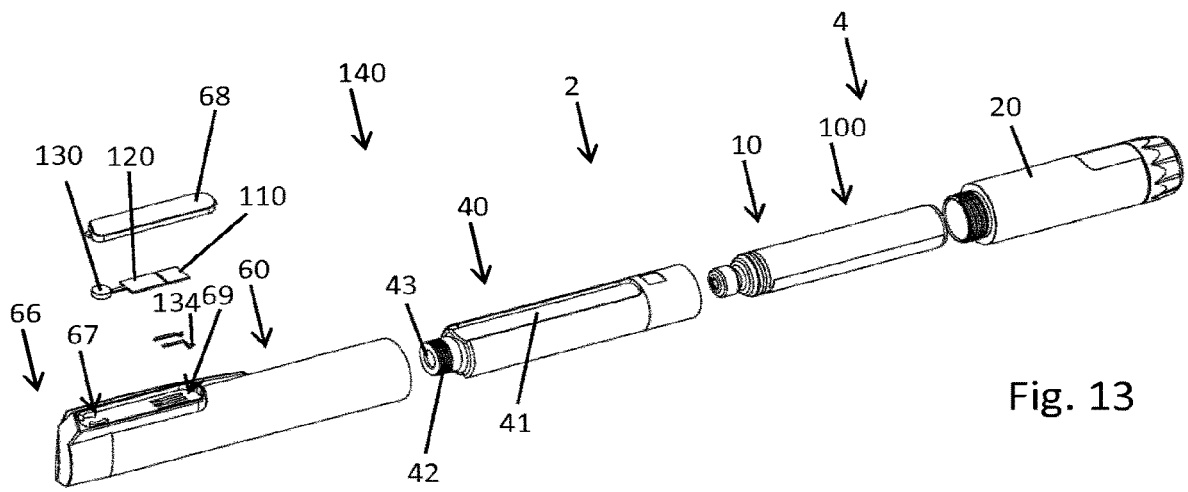
Fig. 13
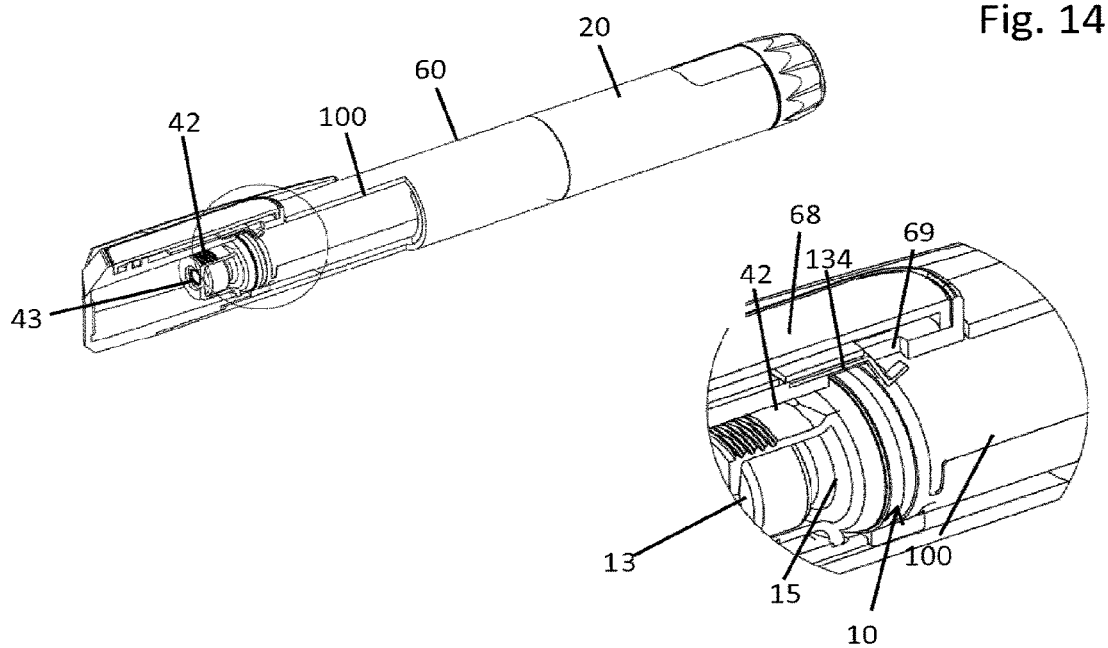
Fig. 14
Fig. 15

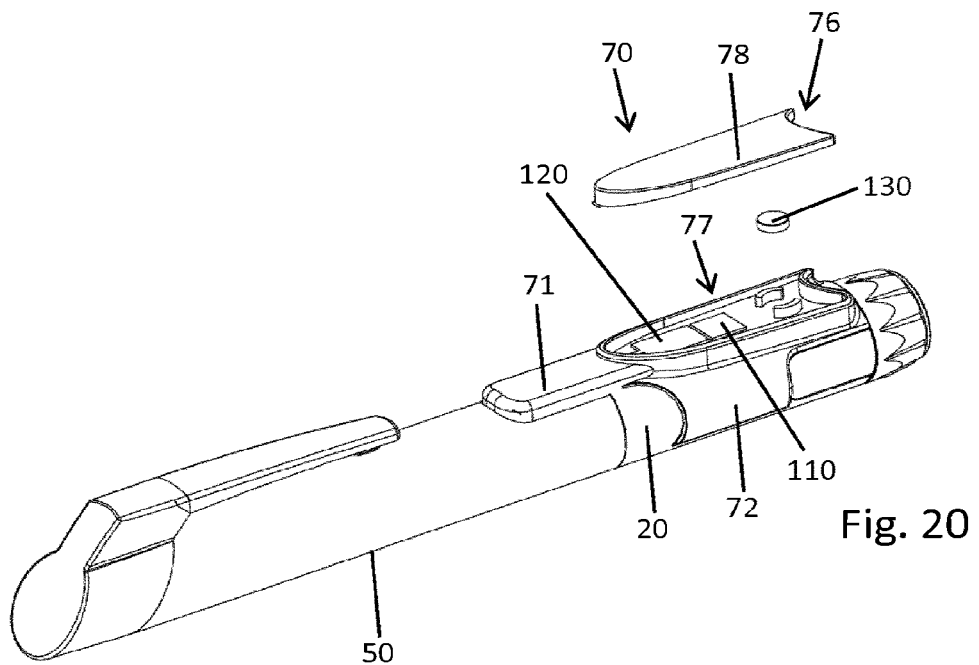
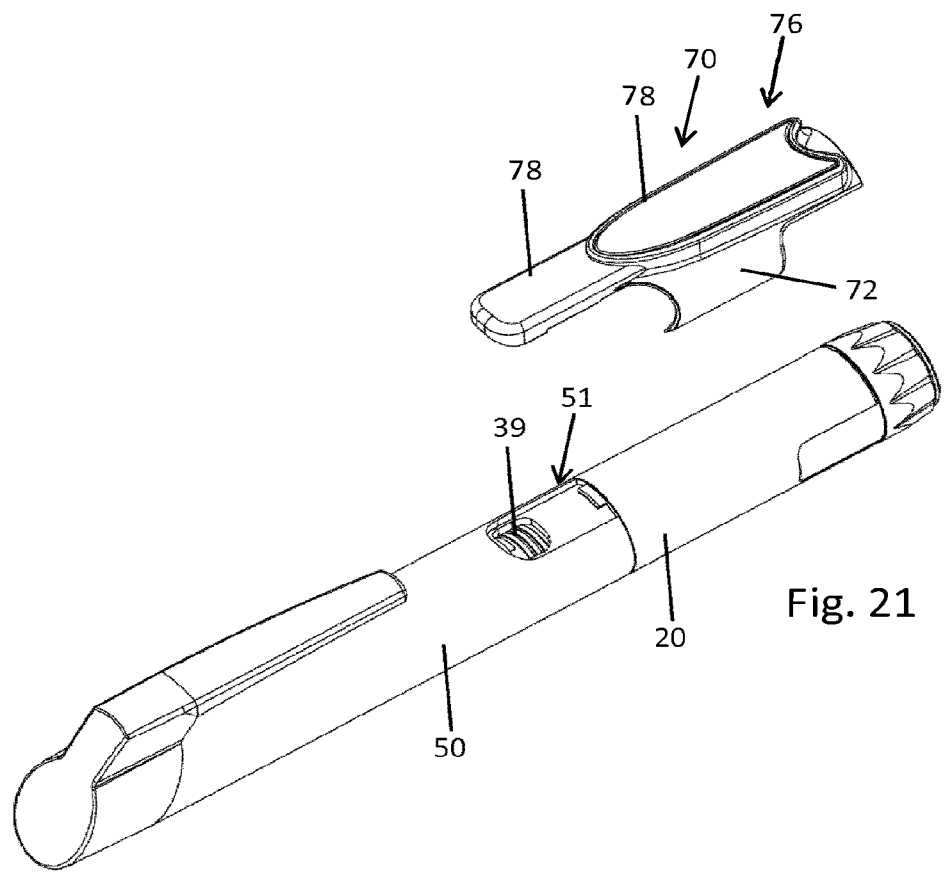

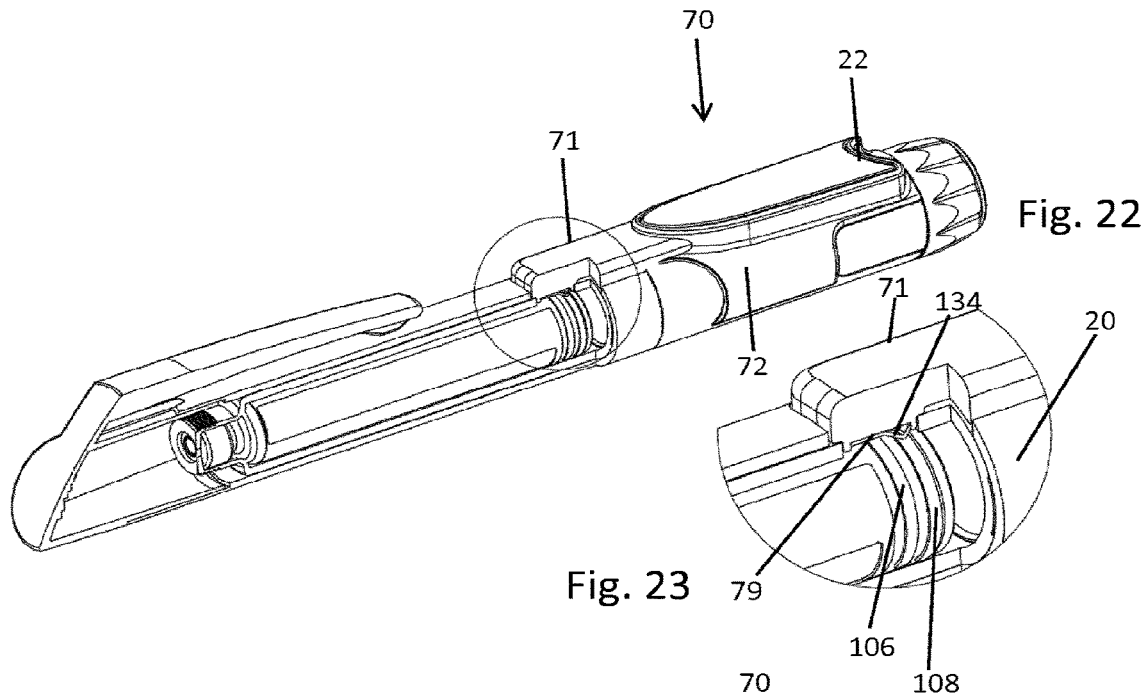
Fig. 22
Fig. 23
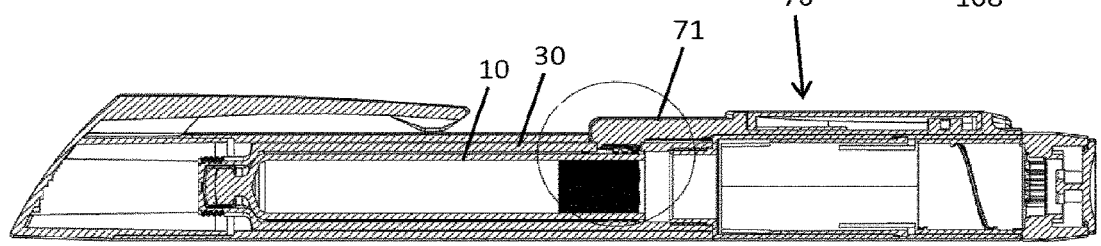
Fig. 24
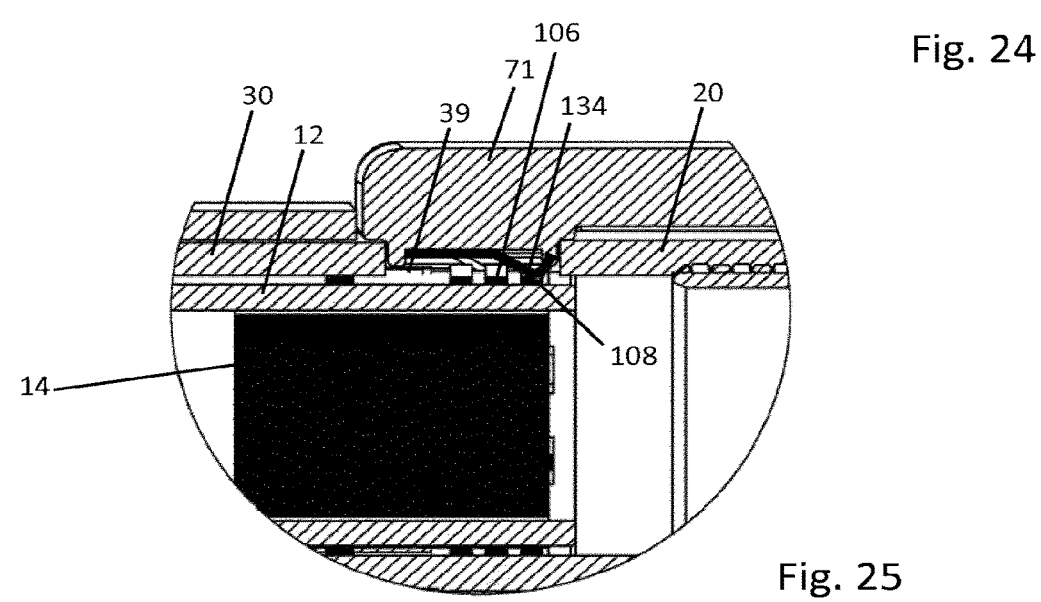
Fig. 25

SENSOR, CARTRIDGE AND DRUG DELIVERY DEVICE

CROSS REFERENCE TO RELATED APPLICATIONS

The present application is a continuation of U.S. patent application Ser. No. 17/116,477, filed on Dec. 9, 2020, which is a continuation of U.S. patent application Ser. No. 15/748,309, filed on Jan. 29, 2018, now U.S. Pat. No. 10,895,487, which is the national stage entry of International Patent Application No. PCT/EP2016/067815, filed on Jul. 26, 2016, and claims priority to Application No. EP 15179216.5, filed in on Jul. 31, 2015, the disclosures of which are expressly incorporated herein in entirety by reference thereto.

TECHNICAL FIELD

The present disclosure relates to the field of measuring at least one physical or chemical parameter of a cartridge filled with a liquid substance, typically filled with a medicament. In addition, the disclosure relates to a cartridge provided with such a sensor. In a further aspect the disclosure relates to a drug delivery device, in particular to an injection device for setting and dispensing of a dose of a liquid medicament.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices such as pen-type injectors have to meet a number of user-specific requirements. For instance, with patients suffering chronic diseases, such as diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been dispensed or used-up.

It is generally desirable to determine the amount of medicament remaining in a cartridge while the cartridge is arranged inside a drug delivery device. It is generally known in the prior art to implement a capacitive measurement or capacitive determination of a filling level of a cartridge. For this either on the cartridge itself or at the interior of a cartridge holder section of the drug delivery device there are provided at least two electrodes. Since the dielectric properties of the liquid substance inside the cartridge clearly differ from those of other surrounding materials, such as the vitreous material the cartridge is made of the rubber-based material forming the proximal piston of the cartridge, the electrical capacity to be measured between the electrodes located on radially oppositely located sidewall portions of the cartridge correlates with the filling level of the cartridge and/or with the axial position of the piston inside the cartridge. The measurable electrical capacity between the electrodes is therefore a direct measure of the axial position of the cartridge's piston. In this way the measured capacity is directly indicative of the cartridge's filling level.

For instance, document WO 2014/052997 A1 discloses a respective dispensing device having at least one pair of capacitive measuring electrodes that are arranged in the outer region of a medicament container for determining the permittivity of the respective medium in an intermediate region between the measuring electrodes. Furthermore, there is described a shield that is arranged around the container and which surrounds the measurement materials in a sheath-like manner.

The correct arrangement of capacitive electrodes at the outer circumference of such containers or cartridges is rather delicate and cumbersome. The electrodes must be correctly positioned and arranged relative to the cartridge. Once the electrodes have been correctly assembled they require electric contacting with a processor in order to provide measurement and data processing of measured capacity values. Only slight modifications or deviations of the relative positioning of at least two electrodes with respect to each other and/or with respect to the cartridge as well as only slight deviations or modifications of the electrical contact with a processor may have drastic consequences on the measurement results. Such high demands in regard to positioning precision and electrical contacting are hardly achievable in a mass manufacturing environment for producing cartridge- and/or drug delivery devices at low costs.

For conducting a measurement of a physical or chemical parameter of the cartridge on the basis of capacitive electrodes electrical energy must be provided. Passive solutions, e.g. on the basis of RFID transponder technologies are rather sophisticated and may be rather susceptible to electromagnetic or mechanical perturbations. Moreover, a measurement or monitoring of relevant parameters can only be conducted if a suitable energy source, typically in form of a RFID reader, is in close proximity to the cartridge or to the drug delivery device equipped with such a cartridge. In addition, the functionalities of such passive sensor systems with a wireless transfer of electromagnetic energy are rather limited with regard to their processing capabilities and storage capacity, e.g. storing sequences of physical or chemical parameters.

It is therefore an object of the present disclosure to provide an improved sensor for measuring at least one physical or chemical parameter of a cartridge, wherein said cartridge is filled with a liquid substance. The sensor should be manufacturable at low costs and should be configured as a disposable entity. Furthermore, the sensor and its interaction with a drug delivery device should provide a large range of functionalities as well as a rather large storage capacity for capturing and storing electronic data representing measured physical or chemical parameters. In addition, the sensor and its interaction with the drug delivery device should enable a constant or frequent measurement of physical or chemical parameters of the cartridge according to a predefined schedule and independent of an external reader or some other external electronic device configured to communicate with the sensor and/or with the drug delivery device.

SUMMARY

In a first aspect a sensor for measuring at least one physical or chemical parameter of a cartridge or syringe is provided, wherein the cartridge or syringe is filled with a liquid substance. Typically, the cartridge is filled with a liquid medicament.

The sensor comprises a planar flexible foil that is arrangeable to an outer circumference of a barrel of the cartridge or syringe. Furthermore, the sensor comprises at least a first and a second measuring electrode arranged on said foil. The electrodes are typically spatially separated from each other in order to enable an arrangement of first and second electrodes at radially opposite sections of a sidewall of the cartridge. Generally, the measuring electrodes may be of arbitrary shape. When arranged or attached to the outer circumference of the sidewall of the barrel the first and the second measuring electrodes are separated from each other, so that at least a portion of the cartridge and the liquid substance contained therein is located between first and second measuring electrodes. Furthermore, the sensor also comprises at least a first and a second contact electrode arranged on said foil. The first contact electrode is electrically connected to the first measuring electrode and the second contact electrode is electrically connected to the second measuring electrode. In this way the two contact electrodes provide a well-defined electrical contact to an electric energy supply and to a processor or further signal processing means, such as a transceiver that are arranged inside a drug delivery device to provide wireless communication of the processor with external devices.

The first and second contact electrodes particularly provide a wired energy supply to the first and second measuring electrodes. In addition, first and second contact electrodes also provide a wired transfer of electrical signals obtained or generated by the first and/or second measuring electrodes.

First and second contact electrodes provide a well-defined electric interface between the measuring electrodes and at least an electric power supply. Typically, the electric power supply is located outside and remote from the sensor. It is typically arranged inside a drug delivery device or it is typically attached to an outside-facing portion thereof. When the sensor is attached or assembled to the cartridge and when said cartridge is placed inside a drug delivery device the first and second contact electrodes will get in electrical contact with an electric power supply so as to enable a measurement of a physical or chemical parameter of the cartridge.

According to an embodiment the sensor just consists of the planar flexible foil, first and second measuring electrodes and first and second contact electrodes. In this way all further components of a sensor assembly that are necessary for actually measuring the physical or chemical parameter of the cartridge are located remote, e.g. in or at the drug delivery device. Especially with reusable drug delivery devices the sensor can thus be easily implemented as a disposable sensor permanently fastened or fixed to a cartridge. Upon emptying of the cartridge the entire cartridge with the sensor attached thereto is to be discarded. Since the sensor comprises nothing but a planar flexible foil and numerous electrodes and since the sensor is void of any further semi-conducting structures or materials a rather eco-friendly disposal as well as a rather cost efficient production thereof can be provided.

Rather expensive and comparatively spacious components of a sensor assembly can be provided remote outside the sensor but inside or attached to a drug delivery device. Due to the reusable characteristics of such a device typical components of a sensor assembly, such as an electric energy supply, a transceiver for data transmission as well as a processor for signal processing of the signals obtained by the measuring electrodes can be arranged in and permanently attached to the drug delivery device and can be sequentially used with multiple sensors or cartridges equipped with such sensors.

According to another embodiment the first and the second contact electrodes are arranged at a longitudinal end section of the foil. Typically, the planar flexible foil extends in a plane defined by a longitudinal direction (z) and a lateral or circumferential direction (u). Longitudinal and lateral directions typically extend perpendicular with respect to each other. The planar flexible foil is configured to be wrapped around or to be attached to the outer circumference of a sidewall of the barrel of the cartridge. When wrapped around or attached to the cartridge the longitudinal direction of the foil typically extends parallel to the longitudinal or axial direction of the axially elongated cartridge whereas the lateral or circumferential direction of the planar flexible foil extends along the tubular or circular circumference of the cartridge's sidewall.

By arranging first and second contact electrodes at a longitudinal end section of the foil the contact electrodes form a distal or a proximal end of the planar flexible foil. When attached or arranged at the outer circumference of the barrel of the cartridge the first and second contact electrodes are arranged at or near a distal end or at or near a proximal end of the tubular-shaped cartridge. In this way only a distal or proximal end section of the planar flexible foil is occupied by first and second contact electrodes. Consequently, a residual and major portion of the planar flexible foil can be used for the arrangement of the at least first and second measuring electrodes.

According to a further embodiment first and second contact electrodes are arranged at a common longitudinal end section of the foil. For instance, first and second contact electrodes are both arranged near or at a distal end of the foil. Alternatively, the first and second contact electrodes are arranged near or at a proximal end section of the foil.

The terms proximal and distal refer to the intended orientation of the planar flexible foil and the respective cartridge inside the drug delivery device. The distal direction denotes a dispensing end of the drug delivery device. When the drug delivery device is implemented as an injection device the distal end of the drug delivery device faces towards an injection site of a patient. The proximal end or the proximal direction faces in the opposite direction. When implemented as an injection device, such as a pen-type injector, the proximal end of the drug delivery device is operable by a hand of a user so as to configure, to set and to conduct an injection procedure.

In another embodiment first and second contact electrodes are arranged at opposite longitudinal end sections of the foil. In such an embodiment it is conceivable that for instance the first contact electrode is located at a proximal end of the planar flexible foil whereas the second contact electrode is located at a distal end of the planar flexible foil. Here, the at least two contact electrodes form a longitudinal confinement of the planar flexible foil with the at least first and second measuring electrodes positioned therebetween. The specific arrangement and position of first and second contact electrodes on the foil depends on the specific implementation of the entire sensor assembly and the specific configuration of the cartridge and the respective drug delivery device. Typically, first and second contact electrodes are arranged in such a position on the planar flexible foil that an electrical contact is formed between the contact electrodes and the electric energy supply when the cartridge equipped with the planar flexible foil is correctly assembled inside the drug delivery device.

According to another embodiment the first and the second contact electrodes are separated in a longitudinal direction and extend substantially parallel in a lateral or circumferential direction. By separating first and second contact electrodes in longitudinal direction each contact electrode can be electrically connected separately to the electric energy supply, e.g. by means of first and second contact elements that are correspondingly positioned and arranged at a respective axial distance in or at the drug delivery device. Moreover, since first and second contact electrodes extend substantially parallel to each other in the lateral or circumferential direction a ring-shaped contact electrode structure can be formed on the outer circumference of the cartridge when the planar flexible foil is wrapped around the sidewall of the cartridge's barrel.

Typically, the wrap of the planar flexible foil and the lateral or circumferential extension of first and second contact electrodes are such that each electrode almost forms a closed ring along the outer circumference of the cartridge's barrel, wherein said ring is located in a single transverse plane extending substantially perpendicular to the longitudinal or axial direction of the flexible foil's wrap or of the cartridge's barrel. In this way each one of the first and second contact electrodes forms a specific axial contact structure that is rotationally invariant as the cartridge is positioned at an arbitrary orientation in the drug delivery device.

According to a further embodiment first and second electrodes extend almost across the entire lateral dimension of the foil. Typically, the entire lateral dimension of the foil almost exactly matches and corresponds to the outer circumference of the barrel of the cartridge. Typically, the planar flexible foil is wrappable around the outer circumference of the barrel without overlap but by covering almost the entire outer circumference of the barrel. When first and second electrodes extend almost across the entire lateral dimension of the foil a substantially closed first and second electrode structure can be obtained. In this way a rotation invariant contact electrode structure can be provided on the outer circumference of the cartridge.

In other embodiment where for instance at least one of the first and second contact electrodes is wrapped around the cartridge in such a way that a small gap remains between oppositely located lateral ends of the contact electrodes the corresponding contact elements of the drug delivery device have a lateral extension exceeding the lateral gap size. In this way, an electrical contact between the contact elements and the contact electrodes is always provided with any arbitrary rotational orientation of the cartridge relative to the contact elements inside the drug delivery device.

In another embodiment the foil is substantially transparent. Furthermore, at least one of the first and second measuring electrodes or at least one of the first and second contact electrodes comprise a printed or coated conductive structure on the foil or in the foil.

The foil itself is typically electrically insulating. In this way the foil actually acts as a flexible planar substrate or as a mechanical support for both the at least first and second measuring electrodes as well as for the at least first and second contact electrodes. By having all electrodes printed or coated on or in the planar flexible foil the various electrodes, namely the first and second measuring electrodes as well as the first and second contact electrodes are inherently correctly positioned relative to each other. A relative position and/or relative orientation of first and second measuring electrodes as well as of first and second contact electrodes permanently persists and may only be subject to a well-defined modification as the initially planar flexible foil is wrapped around the outer circumference of the cartridge's barrel.

The electrodes may comprise a suitable conductive material, such as aluminum, gold, silver or mixtures and alloys thereof. The electrodes may be printed on the flexible foil, e.g. by way of screen printing. Alternatively, they may be coated on the planar flexible foil by any suitable thin film-depositing technology, such as sputtering, spray coating or by means of various chemical vapor-depositing techniques. The foil typically comprises or is made of a transparent polymer. The foil may comprise at least one or a combination of the materials: polycarbonate, polyamide or polyvinyl chloride (PVC).

According to a further embodiment the first and second measuring electrodes and the first and second contact electrodes are located on a common side of the foil. Alternatively, the first and second measuring electrodes are located on one side of the foil and the first and second contact electrodes are located on an opposite side of the foil. The first and second measuring electrodes are always located on the same side of the foil. Also, first and second contact electrodes are always located on the same and common side of the flexible foil.

The first and second contact electrodes are typically arranged on an outside-facing side of the planar flexible foil when the foil is wrapped around the outer circumference of the barrel of the cartridge. With such a configuration it is generally conceivable that the measuring electrodes are also located on the outside-facing side of the wrapped foil. When implemented as capacity measuring electrodes the planar flexible foil is dielectric or permeable to dielectric charges.

In another embodiment it is conceivable that the at least first and second contact electrodes are located on an outside-facing portion of the wrapped foil whereas the at least first and second measuring electrodes are located on an inside-facing portion of the wrapped foil. In such an embodiment it is conceivable that the planar flexible foil comprises a multilayer structure, wherein at least one conductor electrically connecting the first measuring electrode with the first contact electrode extends through the planar flexible foil.

In another embodiment the at least two measuring electrodes are configured as electrical capacity measuring electrodes or as temperature measuring electrodes. When implemented as electrical capacity measuring electrodes the first and the second measuring electrodes typically extend all along the longitudinal extension of the cartridge when the foil is wrapped around the cartridge's barrel. The measuring electrodes may comprise a substantially rectangular structure with a lateral or circumferential extension that is less than half of the circumference of the tubular-shaped barrel. Typically, first and second measuring electrodes are of substantially identical geometric shape.

Apart from a substantially rectangular structure the measuring electrodes may also comprise a tapered structure in axial direction. Moreover, the electrodes might be trapezoidal, triangular or may comprise a combination of a rectangular and a triangular shape. Especially by making use of electrodes having a geometric structure changing constantly in axial direction a respective linearly changing capacity signal is obtainable as for instance the piston of the cartridge is subject to a linear axial displacement in the course of a dispensing procedure. The geometric shape of the electrodes may hence improve the accuracy and precision of the capacity measurement.

Moreover, it is conceivable that there are arranged multiple measuring electrodes along the longitudinal extension of the planar flexible foil, wherein pairs of measuring electrodes located at the same or at overlapping longitudinal positions are pair-wise connectable to a specific processor. By means of multiple pairs of first and second measuring electrodes, wherein said pairs are arranged at different longitudinal positions along the outer circumference of the cartridge's barrel a spatial resolution of an electric capacity measurement and hence a rather high spatial resolution of a position of a piston can be measured and determined by a processor connectable to the various pairs of measuring electrodes.

When implemented as temperature measuring electrodes the electrodes may comprise pairs of heaters and thermistors that are pair-wise and alternately arranged in longitudinal direction along the cartridge's sidewall. Typically, the first measuring electrode may comprise several parallel oriented but longitudinally separated heaters whereas the second electrode may comprise correspondingly arranged thermistors placed longitudinally between the heaters of the first measuring electrode. By means of the first electrode thermal energy can be deposited to the sidewall of the cartridge and by means of the various thermistors, hence by means of the second electrode, temperature irregularities caused by the position of the piston inside the cartridge can be measured and determined. Typically, each branch of first and second electrodes forming a heater or a thermistor is separately connectable to a processor of the sensor assembly. In this way a thermal excitation and a heat transfer across the sidewall of the cartridge can be monitored with a spatial resolution in accordance to the distance of neighboring branches of first and second electrodes. When configured and implemented as temperature measuring electrodes the measuring electrodes act as a thermal sensing array or like a thermal flow sensor.

Implementation of such a temperature measuring arrangement is of particular benefit when sufficient electrical power can be supplied by the electric energy supply. By implementing the electric energy supply in the drug delivery device, e.g. in form of a battery, a solar cell or combinations thereof, sufficient electrical power for a temperature measurement can be easily provided in a rather cost efficient way.

According to another aspect the disclosure relates to a cartridge comprising a tubular-shaped barrel filled with a liquid substance, typically filled with a liquid medicament. The cartridge further comprises a sensor as described above which is wrapped around the outer circumference of the sidewall of the barrel.

The cartridge to which the sensor is arrangeable or attachable may comprise a tubular-shaped barrel, e.g. made of glass or some other material substantially inert to the liquid substance contained therein. The cartridge may comprise a distally-located and pierceable outlet sealed by a pierceable septum so as to obtain access to the interior of the cartridge by way of puncturing the distal seal by means of a piercing assembly, such as a double-tipped injection needle. Opposite the distal outlet the cartridge, in particular its tubular-shaped barrel, is typically sealed by a piston slidably displaceable inside the cartridge. The piston is slidably displaceable in distal direction relative to the barrel under the effect of a distally-directed driving force, typically exerted by a plunger or piston rod of the drug delivery device advancing in distal direction, thereby exerting a distally-directed pressure to said piston. The sensor is particularly dedicated to such cartridges but could also be used otherwise, e.g. for other types of medicament containers, including vials, ampoules, bottles or flexible bags.

The assembly of cartridge and sensor may be configured as a disposable unit, which after consumption or dispensing of the content of the cartridge is to be discarded in its entirety. Typically and since the flexible foil of the sensor is substantially transparent, a filling level of the cartridge is also visually inspectable even when the sensor, hence the flexible foil with electrodes thereon is attached to the cartridge. The electrodes may also be of transparent type. For instance, the electrodes may comprise or may consist of indium-tin oxide (ITO) that is conductive and substantially transparent. The visual inspectability of the interior of the cartridge even with the sensor completely covering the cartridge's sidewall is of particular benefit in order to provide an intuitive control whether the content of the cartridge, in particular the liquid medicament, might be subject to coagulation or flocculation or some other detrimental effects or phenomena.

In another embodiment the sensor is permanently attached to the cartridge and covers the complete tubular-shaped sidewall portion thereof. In such a configuration it may be of particular benefit when the sensor, in particular the planar flexible foil is provided with a visual scale that may be persistently printed on an upper side or lower side of the flexible foil. The scale may comprise various symbols, numbers or other signs in order to visually display a momentary filling level of the cartridge. By providing a scale, e.g. with numerous equidistantly arranged scale items typically separated along the axial or longitudinal direction of the flexible foil there is no longer a need to provide such scale items directly on the outer circumference of the, e.g. vitreous barrel. By providing a visual scale on the sensor, in particular on the flexible foil of the sensor and by attaching the sensor in a well-defined, precise and highly reproducible way on the outer circumference of the cartridge's barrel a rather cost efficient, straight forward and easy way of providing visually perceptible scale items on a vitreous barrel is provided.

According to a further embodiment the sensor, in particular its planar flexible foil is adhesively attached to the barrel of the cartridge. The adhesive agent for the adhesive attachment of sensor and cartridge may be provided on one side of the foil that faces radially inwardly as the foil is wrapped around the tubular-shaped cartridge.

The adhesive may be located on a side of the foil opposite to the first and second measuring electrodes. In such a configuration the measuring electrodes are located on an outside-facing side of the foil facing radially outwardly as the foil is wrapped around the cartridge. Alternatively, it is also conceivable that the measuring electrodes are located on an inside-facing portion of the wrapped foil. Then, the adhesive agent may be located longitudinally and/or circumferentially between the measuring electrodes. It is also conceivable, that the adhesive is located radially between the outer circumference of the barrel of the cartridge and the measuring electrodes of the sensor as the sensor is wrapped around the barrel.

According to another embodiment the contact electrodes of the sensor are located on an outwardly-facing side of the foil as the sensor is wrapped around the tubular-shaped barrel. In this way the contact electrodes are easily accessible from outside the cartridge for establishing an electrical connection between first and second measuring electrodes and at least the electric energy supply, the processor and/or a transceiver of the sensor assembly.

According to another aspect the disclosure further relates to a drug delivery device for administering a dose of a liquid medicament. The drug delivery device comprises a housing to accommodate a cartridge as described above, wherein the cartridge is filled with the liquid medicament and comprises a piston slidably received in the barrel of the cartridge. The drug delivery device further comprises a drive mechanism typically having a piston rod or a plunger to exert a distally-directed driving force on the piston of the cartridge for expelling of a dose of the liquid medicament via a distally-located outlet of the cartridge. The outlet of the cartridge is connectable with a piercing assembly, typically comprising a double-tipped injection needle by way of which fluid transferring access to the interior of the cartridge is obtainable and by way of which the medicament expelled from the cartridge can be directly injected into biological tissue.

Typically, the drug delivery device is configured as an injection device, such as a pen-type injector that provides individual and variable setting and subsequent dispensing of a dose of a medicament of variable and user-settable size.

Furthermore, the drug delivery device comprises an electrical energy supply electrically connectable to the first and second contact electrodes of the sensor when the sensor attached to the cartridge is located inside the drug delivery device. The drug delivery device further comprises a processor connected to the electrical energy supply. The processor is configured to obtain and to process electrical signals obtainable from the sensor as the sensor is supplied with electrical energy when in electrical contact with the electrical energy supply. The processor, e.g. configured as microcontroller, comprises a storage or a memory to store a sequence of measurement data. In addition, the processor is typically programmable so as to automatically conduct various measurement routines, e.g. in accordance with a predefined schedule. For instance, the processor may be programmed to conduct and to initiate temperature and/or content measurements of the cartridge at regular time intervals, such as several times a day, for instance every second hour. In this way environmental parameters, such as the temperature the cartridge is exposed to can be sequentially and constantly monitored.

In addition, the drug delivery device also comprises a transceiver connected to the processor. The transceiver is configured for wireless communication with an external device, such as a computer, a tablet computer, a mobile phone, a smartphone or a smartwatch or comparable personal electronic devices. The transceiver may be implemented as a radio-frequency (RF) transponder to communicate with the external electronic device via standardized communication protocols, such as Bluetooth, Wi-Fi or NFC. Alternatively, the transceiver may be implemented as an optical transmitter, e.g. operating in the infrared spectral range. In such a configuration the transceiver may comprise an IRDA interface. The arrangement of transceiver and processor may constitute or form an active RFID chip or an active RFID tag that is electrically powered by the electrical energy supply.

According to another embodiment the housing of the drug delivery device comprises a cartridge holder in which the cartridge is assembled. When implemented as a reusable device the housing of the drug delivery device typically comprises a proximally-located body releasably connectable to a distally-located cartridge holder. By disconnecting or by releasing cartridge holder and body a cartridge can be assembled inside the cartridge holder. As the medicament contained in the cartridge has been completely dispensed the cartridge can be replaced by a new one. For this the cartridge holder can be disconnected or released from the housing.

After exchanging an empty cartridge from the proximal end of the cartridge holder by a new one the cartridge holder can be re-attached or re-assembled to the body of the housing. Moreover, and according to a further embodiment, the drug delivery device is configured as a disposable device. Here, the cartridge with the sensor attached thereto is readily and initially arranged inside a cartridge holder, which cartridge holder is irreleasably and hence permanently connected to the body of the housing. In the present context an irreleasable connection means a connection non-detachable connection that is only separable by brute force methods and by destroying the integrity of at least one of cartridge holder and housing of the drug delivery device.

When implemented as a disposable device it is of particular benefit that electronic components of the sensor assembly, hence the processor, the electric energy supply as well as the transceiver are located in a separate accessory device that is detachably connectable to the housing of the drug delivery device. In this way the sensor assembly can be repeatedly used and attached to various disposable drug delivery devices on demand.

In another embodiment the transceiver and the processor are configured as a passive RFID chip or passive RFID tag. Here, the transceiver is operable and/or configured to withdraw and to obtain electrical energy from a RF field in the vicinity and to provide electrical energy to the processor and/or to the electrodes in order to conduct a measurement and/or to process measurement data obtained from the contact electrodes and/or to transmit the measured or processed data to another electronic device.

In effect, the sensor assembly can be implemented as a hybrid-type of active and passive RFID of NFC assembly. It may be constantly powered by the electrical energy supply, e.g. for a regular storage of data at predefined time intervals and independent of the presence of a RF field in close vicinity. In addition, the sensor assembly can be configured to obtain and to derive electrical energy via the transceiver when exposed to a RF field that may be provided and generated by an external electronic device, such as a smartphone. Such a passive behavior may be of particular use to save energy and to optimize the power management of the device. The battery lifetime could be prolonged in this way.

It is of particular benefit when the processor and the transceiver are configured to switch into a passive mode per default and to operate as long as possible on the basis of electrical energy derived from an applied RF field. In situations where a suitable RF field is not present the processor may conduct or trigger a measurement procedure on the basis of electrical energy obtained from the electrical energy supply, e.g. from a battery. It is also conceivable that the electrical energy supply, hence a battery, constantly keeps the processor powered, e.g. for monitoring the status or a dose history of the cartridge or syringe. Only when obtaining additional electrical power from a RF field the processor and the transceiver will then communicate wirelessly with an external electronic device. Such an approach would be fery energy efficient thus prolonging the lifetime of a battery.

According to a further embodiment the drug delivery device also comprises at least one operating element electrically connected to the energy supply to the processor or the transceiver to initiate a sensor-based measurement or to initiate a communication with an external electronic device by means of the transceiver. The operating element is user-actuatable. It may comprise a push button or a dial that is user-actuatable in order to trigger a measurement or a communication, e.g. a data exchange with the external electronic device. Additionally or alternatively, the operating element may be also software implemented in the external electronic device. Upon establishing a communication link between the external electronic device and the processor of the sensor assembly the operating element may be presented as a user selectable menu item, e.g. on a display of the external electronic device.

By means of the operating element a manual and user-actuatable measurement of the at least one physical or chemical parameter of the cartridge and in particular of the liquid substance contained therein can be triggered and initiated on request.

According to another embodiment the electrical energy supply comprises a compartment housing a battery and a first and a second contact element, each of which being electrically connectable to the battery. First and second contact elements further extend through a through opening of the housing to electrically connect with the first and with the second contact electrodes of the sensor, respectively. Typically, the compartment is accessible from outside via a detachable or releasable closure. Detaching or opening of the closure provides access to the interior of the compartment. In this way an empty battery could be exchanged or replaced by a new one. Additionally or alternatively, the battery may be rechargeable battery and the electrical energy supply may be further equipped with a solar cell or with some other kind of recharging means to accumulate, to generate and to store electrical energy in the battery.

In a further embodiment the compartment is integrated into a cartridge holder, in a protective cap detachably covering at least a distal end of the cartridge holder or the compartment is integrated in an accessory device detachably connectable to the housing. Typically, the accessory device may comprise at least one fastening clip by way of which the accessory device is detachably connectable to a particular portion of the housing of the drug delivery device. The accessory device is attachable to a body of the housing of the drug delivery device. Here, the accessory device may extend towards and to radially overlap with the cartridge holder of the housing of the drug delivery device. So when the compartment is integrated into the cartridge holder or in the accessory device it is the cartridge holder that comprises a through opening in a sidewall portion so that an electrical contact between first and second contact electrodes of the sensor attached to the cartridge and first and second contact elements of the electrical energy supply can be provided.

In an alternative embodiment the compartment is integrated into a protective cap detachably covering at least a distal end of the cartridge holder. Here, the protective cap as well as the cartridge holder comprise a through opening through which an electrical contact between first and second contact elements of the electrical energy supply and first and second contact electrodes of the sensor can be established, respectively.

The term 'sensor assembly' as used herein defines a system including the sensor with measuring electrodes and contact electrodes, an electric energy supply, a processor and a transceiver. Operation and completion of the sensor assembly is obtained as the cartridge equipped with the sensor is assembled inside the drug delivery device, thereby establishing electrical contact between the first and second contact electrodes and the electric energy supply.

Typically, at least the planar flexible foil with first and second measuring electrodes and with at least first and second contact electrodes is assembled and permanently fastened to the cartridge whereas other electronic components of the sensor assembly are assembled in the drug delivery device or wherein such electronic components are attached to the drug delivery device. In this way the sensor assembly can be split and separated among various components of the drug delivery device, namely the housing of the drug delivery device and the cartridge that may be replaceable or exchangeable.

The sensor and its planar flexible foil may be implemented as a kind of a label, which in addition to the measuring capability of at least one physical or chemical parameter of the cartridge is also operable to label or to distinguish the cartridge from other identically shaped cartridges. As the electric energy supply is integrated into the drug delivery device it does not have to be provided on said label. In this way the label can be kept small and requires only a minimum of space. Driving of the sensor by means of an electric energy source located remote from the sensor allows for a relatively complex and multifunctional sensor implementation.

The remotely-located electrical energy supply, e.g. comprising a battery, provides and enables sensor functionalities such as the creation of a dose history which may be stored in the processor or in a separate memory cell connected to the processor. On demand, a captured or recorded dose history can be transmitted to an external electronic device, such as a smartphone or a computer via the transceiver of the sensor assembly. It is generally to be mentioned that the sensor is not only capable to determine the filling level of the cartridge but that the electrodes thereof may be configured to conduct optical transmission measurements so as to inspect cloudiness, formation of aggregations, or the mixing status of constituted lyophilisates contained inside the cartridge. In such embodiments it is conceivable that at least one of the first and second measuring electrodes comprises a photo detector whereas the other one of first and second electrodes is implemented as a light transmitting device.

By arranging the electric energy supply and the transceiver in or on the drug delivery device the energy supply and the transceiver can be of reusable type whereas the sensor attached to the cartridge may be of disposable type. By establishing an electric contact between the electric energy supply and the sensor upon assembly of the cartridge inside the drug delivery device the processor can be permanently or frequently powered as long as the cartridge is positioned inside the drug delivery device. In this way the processor and the sensor can be operated to permanently collect and to permanently or frequently capture or store cartridge-related data during the entire lifetime of the cartridge. Such data may include the dose history as well as the temperature history of the cartridge. A wireless transmission of collected data may be frequently conducted either on external request or regularly according to a predefined schedule, e.g. stored in the processor.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39); or des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6—NH2,
H-(Lys)6-des Pro36, Pro37, Pro38 [Asp28] Exendin-4(1-39)-(Lys)6—NH2,
H-Asn-(Glu)5-des Pro36, Pro37, Pro38 [Asp28] Exendin-4(1-39)-(Lys)6—NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(02)25, Asp28] Exendin-4(1-39)-(Lys)6—NH2,
H-(Lys)6-des Pro36, Pro37, Pro38 [Trp(02)25, Asp28] Exendin-4(1-39)-(Lys)6—NH2,
H-Asn-(Glu)5-des Pro36, Pro37, Pro38 [Trp(02)25, Asp28] Exendin-4(1-39)-(Lys)6—NH2,
H-(Lys)6-des Pro36 [Met(0)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(0)14, Asp28] Exendin-4(1-39)-NH2,
H-Asn-(Glu)5-des Pro36, Pro37, Pro38 [Met(0)14, Asp28] Exendin-4(1-39)-NH2,
des Pro36, Pro37, Pro38 [Met(0)14, Asp28] Exendin-4(1-39)-(Lys)6—NH2,
H-(Lys)6-des Pro36, Pro37, Pro38 [Met(0)14, Asp28] Exendin-4(1-39)-(Lys)6—NH2,
H-Asn-(Glu)5 des Pro36, Pro37, Pro38 [Met(0)14, Asp28] Exendin-4(1-39)-(Lys)6—NH2,
H-Lys6-des Pro36 [Met(0)14, Trp(02)25, Asp28] Exendin-4(1-39)-Lys6-NH2,
H-des Asp28 Pro36, Pro37, Pro38 [Met(0)14, Trp(02)25] Exendin-4(1-39)-NH2,
H-(Lys)6-des Pro36, Pro37, Pro38 [Met(0)14, Asp28] Exendin-4(1-39)-NH2,
H-Asn-(Glu)5-des Pro36, Pro37, Pro38 [Met(0)14, Trp (02)25, Asp28] Exendin-4(1-39)-NH2,
des Pro36, Pro37, Pro38 [Met(0)14, Trp(02)25, Asp28] Exendin-4(1-39)-(Lys)6—NH2, H-(Lys)6-des Pro36, Pro37, Pro38 [Met(0)14, Trp(02)25, Asp28] Exendin-4(S1-39)-(Lys)6-NH2, H-Asn-(Glu)5-des Pro36, Pro37, Pro38 [Met(0)14, Trp (02)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as it is defined by the claims. Further, it is to be noted, that any reference numerals used in the appended claims are not to be construed as limiting the scope of the invention.

BRIEF DESCRIPTION OF THE FIGURES

In the following, an embodiment of the display arrangement, the drive mechanism and the drug delivery device is described in detail by making reference to the drawings, in which:

FIG. 1 schematically shows one embodiment of a drug delivery device implemented as a pen-type injector, FIG. 2 schematically shows a cartridge and a sensor to be attached thereto, FIG. 3 is an isolated illustration of the sensor, FIG. 4 shows a longitudinal end of the sensor in an enlarged view, FIG. 5 shows the drug delivery device according to FIG. 1 in an exploded view, FIG. 6 shows the device according to FIG. 1 with the distal housing sections partially cut away, FIG. 7 is an enlarged view of a section of FIG. 6, FIG. 10 shows another embodiment of a sensor, FIG. 11 shows an alternative way of attaching the sensor to a cartridge, FIG. 12 is an isolated and perspective view of a cartridge equipped with a sensor wrapped around the cartridge, FIG. 13 shows another embodiment of the drug delivery device in an exploded perspective view, FIG. 14 shows the drug delivery device according to FIG. 13 with the distal housing components partially cut away, FIG. 15 is an enlarged view of a section of FIG. 14, FIG. 20 shows the drug delivery device according to FIG. 18 with an opened compartment, FIG. 21 shows the device according to FIG. 18 with the accessory device separated from the body of the drug delivery device, FIG. 22 shows the device according to FIG. 18 with distal housing sections of the device partially cut away, FIG. 23 is an enlarged view of a section of FIG. 22, FIG. 24 shows a longitudinal cross-section through the device according to FIG. 22 and FIG. 25 is an enlarged view of a section of the illustration according to FIG. 24.

DETAILED DESCRIPTION

Figure 8:
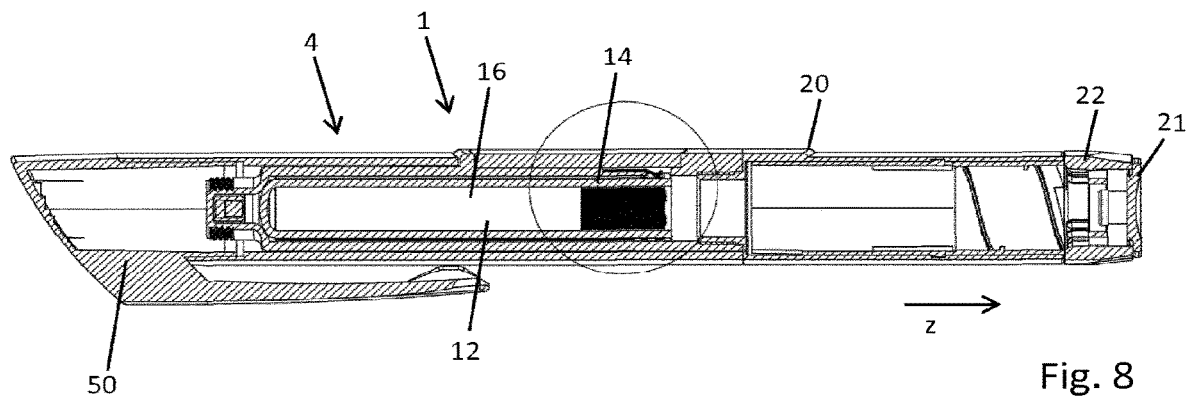
FIG. 8 is a longitudinal cross-section through the device according to FIG. 1.

The drug delivery device 1 as illustrated for instance in FIG. 1 is implemented as a pen-type injector. The drug delivery device 1 is a handheld drug delivery device. It comprises a housing 4, which housing 4 comprises various parts. As shown in FIG. 5, the housing 4 actually includes or comprises a cartridge holder 30 and a body 20. Both, the cartridge holder 30 as well as the body 20 are of substantially tubular shape. As illustrated in the various FIGS. a proximal end of the cartridge holder 30 is connectable to a distal end of the body 20. The cartridge holder 30 comprises a window 31 in a sidewall allowing to visually inspect the cartridge 10 to be assembled therein.

At its distal end the cartridge holder 30 comprises a threaded socket 32. At its distal end face the cartridge holder 30 further comprises a through opening 33 through which a proximally-extending tipped end of a double-tipped injection needle may extend in order to pierce a distal seal 13 of the cartridge 10. In FIG. 5 the proximal direction is denoted P and the distal direction is denoted D. The cartridge 10 as shown in FIG. 2 comprises a tubular-shaped barrel 11 having a tubular-shaped sidewall 12, which in distal direction D extends into a stepped down neck portion 15. At the distal end of the stepped down neck portion 15 there is provided a pierceable seal 13, typically implemented as a pierceable septum.

The proximal end of the cartridge 10 is sealed by a piston 14 as illustrated in FIG. 8. The piston 14 is frictionally engaged with the inside-facing portions of the sidewall 12 of the barrel 11 of the cartridge 10. The piston 14 is slidably received inside the barrel 11 of the cartridge 10. When assembled inside the cartridge holder 30 the vitreous barrel 11 of the cartridge 10 is visually inspectable through the window 31 of the cartridge holder 30. The cartridge 10 is axially secured or axially fastened inside the cartridge holder 30 through an axial abutment of the radially narrowing neck portion 15 getting in axial abutment with a correspondingly-shaped diameter-reduced socket 32 of the cartridge holder 30. The threaded socket 32 is threadedly engageable with a correspondingly-threaded needle hub that is releasably and detachably connectable to the cartridge holder 30 for dispensing of a dose of the medicament 16 located inside the cartridge.

As the cartridge 10 is arranged and fixed inside the cartridge holder 30 and when the cartridge holder 30 is attached to the body 20 a drive mechanism 5 of the drug delivery device 1 located inside the body 20 is operable to exert distally-directed thrust to the piston 14 so that a well-defined dose of the liquid substance or medicament 16 can be expelled from the cartridge 10 via the injection needle or piercing assembly in fluid communication with the interior of the cartridge 10.

Typically, the drive mechanism 5 comprises at least a piston rod to advance in distal direction D. The drive mechanism 5 may be implemented in many different ways. It may be fully mechanically implemented so that a driving force acting on the piston 14 is exclusively provided e.g.by a thumb of a user actually depressing a proximally protruding dispensing button 21 located at a proximal end face of the body 20. In addition there may be provided a dose dial 22 by means of which a user may individually set a dose of variable size. Additionally, the drive mechanism 5 typically comprises a dose indicating window through which a rotatable dose indicating scale is visible.

Other implementations of the drive mechanism 5 may include a power-assisted dispensing. There, a driving force for advancing the piston rod in distal direction D may be provided or supported by a mechanical energy storage means, such as a spring, which may be pre-tensed upon a final assembly of the drug delivery device 1. It is also conceivable, that a mechanical energy storage means, such as a spring is repeatedly biased during a dose setting procedure. In this case, dialing of the dose dial 22 serves to bias or to stress a dispensing spring. Further implementations of the drive mechanism 5 may include electromechanical means, such as electric drives that are operable to assist or to contribute to the advancing motion of the piston rod. Alternatively, the dispensing force acting on the piston or on the respective piston rod may be completely provided by a respective electrical drive.

As it is apparent from FIGS. 2 and 5 there is provided a sensor 100 having a planar flexible foil 110 which is wrappable around the outer circumference of the barrel 11 of the cartridge 10. The sensor 100 is part of a sensor assembly 140 and serves to measure at least one physical or chemical parameter of said cartridge 10. Typically, the sensor 100 is implemented as a fill level sensor to measure the fill level of the cartridge, typically by way of determining and by way of measuring the actual axial position of the piston 14 inside the cartridge 10. In addition or alternatively, the sensor 100 is implemented as a temperature sensor.

The sensor 100 comprises at least a first and a second measuring electrode 102, 104. The measuring electrodes 102, 104 extend substantially parallel along a longitudinal direction (z). They are separated in circumferential direction (u) by a predefined distance that corresponds to the circumference of the sidewall 12 of the barrel 11 of the cartridge 10. Typically, the lateral or circumferential distance between the parallel oriented first and second measuring electrodes 102, 104 is selected such that when the sensor 100 is wrapped around the tubular portion of the sidewall 12 of the cartridge 10 first and second measuring electrodes 102, 104 are diametrically oppositely-located on the outer circumference of the sidewall 12 of the cartridge 10.

In this way, the cartridge 10 and the liquid substance 16 located therein are somewhat sandwiched between the first and the second measuring electrode 102, 104. The planar flexible foil 101 is typically transparent. It is also conceivable that the first and second measuring electrodes 102, 104 are substantially transparent. In this way visual inspection of the vitreous and transparent cartridge 10 is not impeded when the sensor 100 is wrapped around the cartridge 10. In addition to the at least first and second measuring electrodes 102, 104 the sensor 100 further comprises a first and a second contact electrode 106, 108 also arranged on said planar flexible foil 101.

Figure 9:
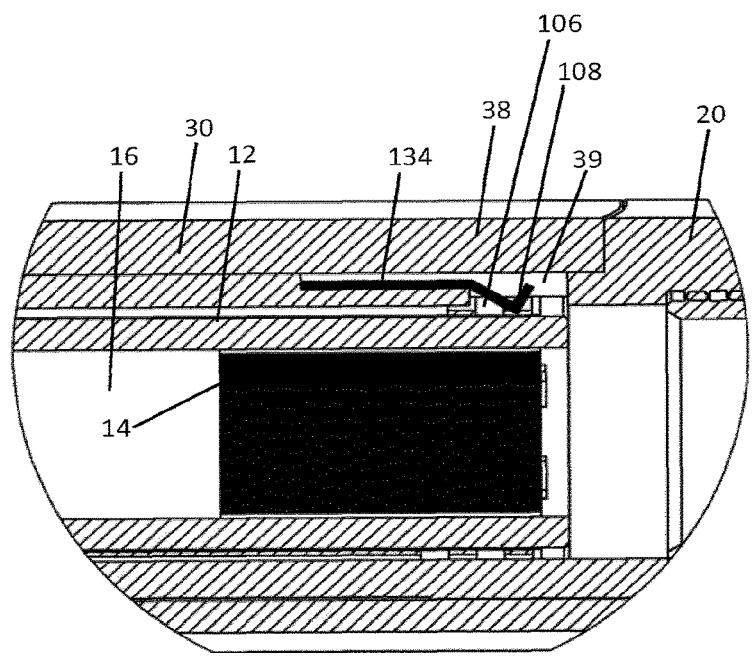
FIG. 9 is an enlarged view of a middle section of the illustration according to FIG. 8.
Figure 16:
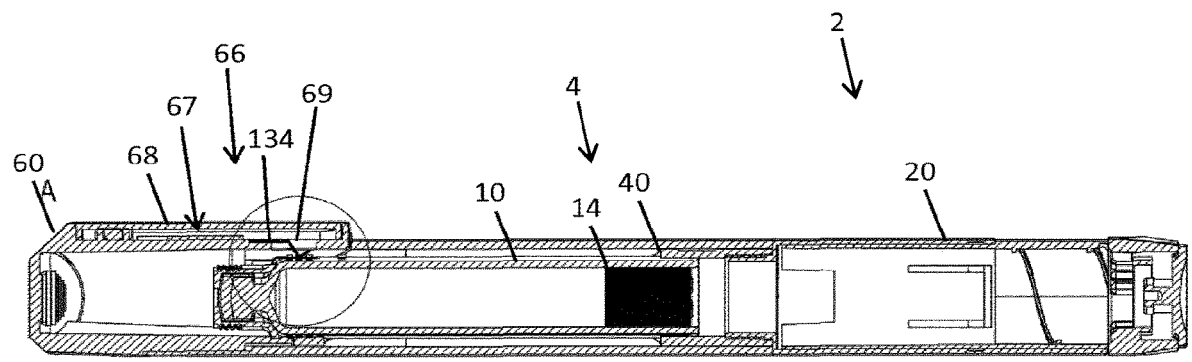
FIG. 16 is a longitudinal cross-section through the device according to FIG. 14
Figure 17:
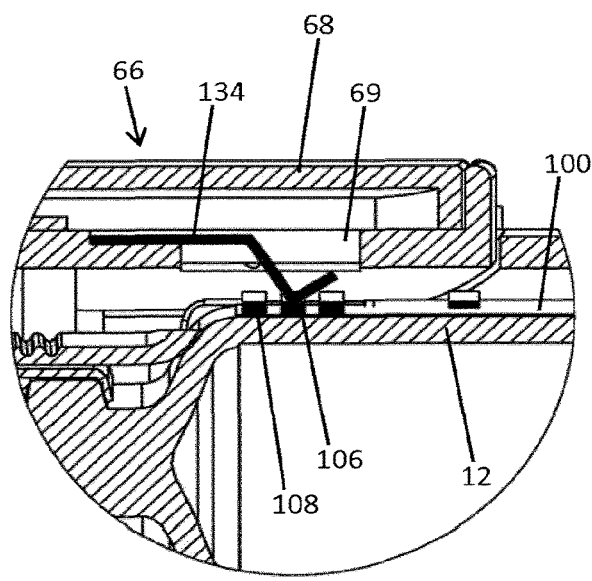
FIG. 17 is an enlarged view of a distal section of FIG. 16.

As it is shown in detail in FIG. 4, first and second contact electrodes extend substantially perpendicular to the elongation of first and second measuring electrodes 102, 104. Moreover, first and second contact electrodes 106, 108 extend along a longitudinal end section 103 of the planar flexible foil 101. First and second contact electrodes 106, 108 are actually separated by a small axial gap. Moreover, first and second contact electrodes 106, 108 comprise a longitudinal straight-lined extension. When the sensor 100 is wrapped around the outer circumference of the sidewall 12 of the barrel lithe first contact electrode 106 as well as the second contact electrode 108 form a substantially closed ring structure. Such a ring structure allows for a rotation invariant arrangement of the cartridge 10 inside the cartridge holder 30 whilst guaranteeing an electric contact to an electric energy supply 36 as for instance shown in FIG. 5, 7 or 9.

The planar flexible foil 101 may be adhesively attached to the outer circumference of the sidewall 12 of the cartridge 10. When attached to the cartridge 10 the first and second contact electrodes 106, 108 are located on an outside-facing side 101b of the foil 101 so as to provide electric contacting from outside the sensor 100. The measuring electrodes 102, 104 may be located on the same side as the contact electrodes 106, 108. Alternatively it is conceivable that at least the first and the second measuring electrodes 102, 104 are located on an inside-facing side 101a of the foil 101. In such an embodiment the measuring electrodes 102, 104 would get in direct mechanical contact with the outer circumference of the sidewall 12 of the cartridge 10.

When the contact electrodes 106, 108 and the measuring electrodes 102, 104 are located on a common side 101b of the foil 101, manufacturing and production of the sensor 100 can be implemented in a rather simple and cost efficient way. For instance, all electrically conductive structures, such as first and second measuring electrodes 102, 104 as well as first and second contact electrodes 106, 108 together with various conductors 105 extending therebetween can be printed or coated in a single step onto the planar flexible foil 101.

Figure 18:
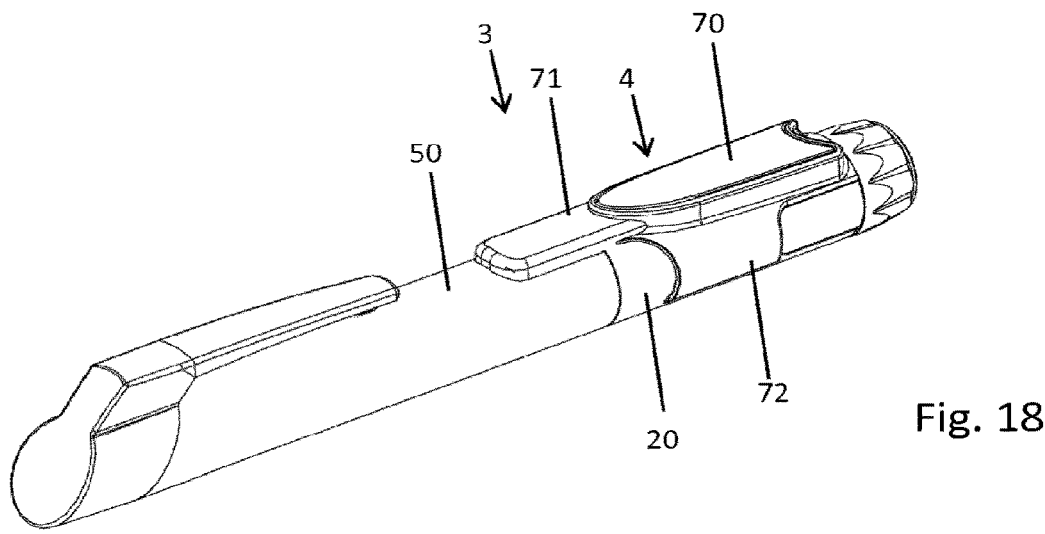
FIG. 18 shows another embodiment of a drug delivery device equipped with an accessory device.
Figure 19:
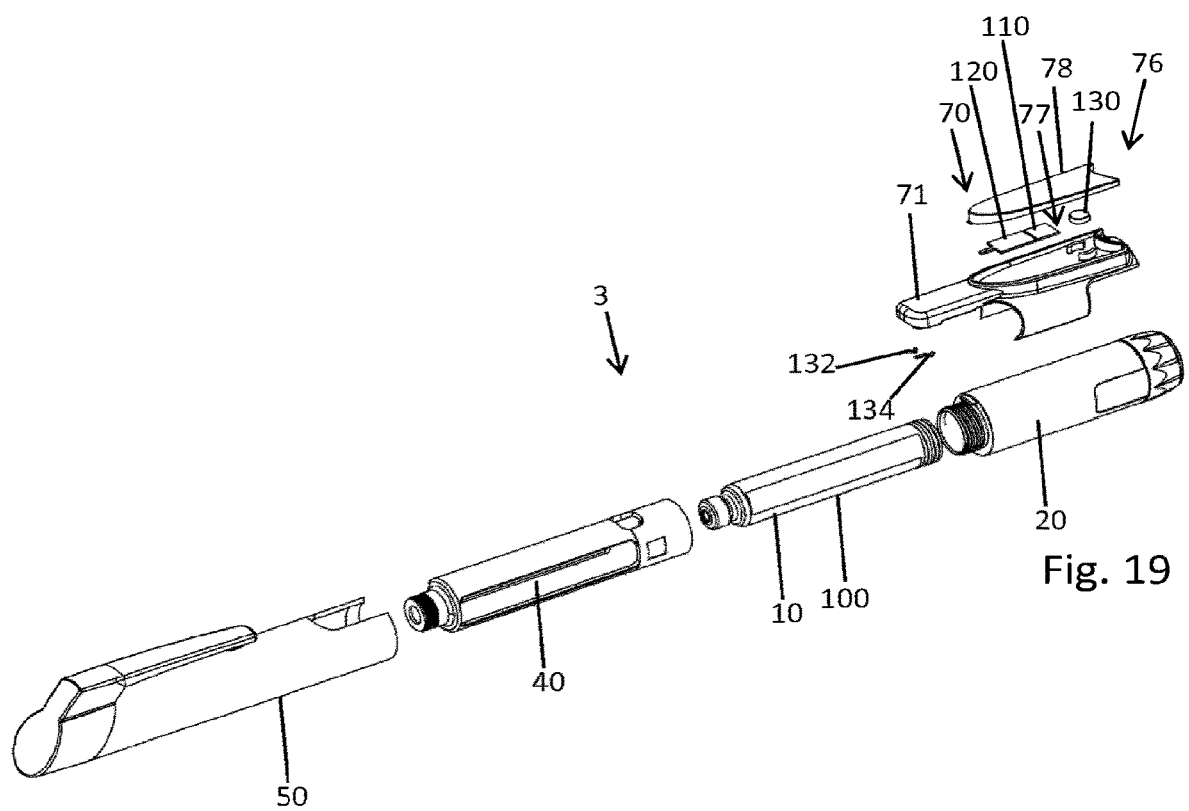
FIG. 19 shows an exploded view of the drug delivery device according to FIG. 18.

The sensor 100 is a component of a sensor assembly 140. The sensor assembly 140 comprises the sensor 100, an electric energy supply 36, a processor 110 and a transceiver 120. In all embodiments as illustrated in the various Figures the sensor 100 only comprises the first and second measuring electrodes 102, 104 as well as the at least first and second contact electrodes 106, 108. All residual components of the sensor assembly 140 are located and arranged in the housing 4 of the drug delivery device 1. In some embodiments, the residual components of the sensor assembly 140 are attached or are attachable to the housing 4 of the drug delivery device 1. The residual components may be arranged inside or at an accessory device 70 that might be fastened to the housing 4 of the drug delivery device 1, e.g. by way of a fastening clip 72 as for instance shown in FIGS. 18 and 19.

At least the electric energy supply 36 is located on or in the housing 4 of the drug delivery device 1. Typically, the electric energy supply 36 comprises at least one battery 130, presently illustrated as a button battery.

The sensor assembly 140 is completed and becomes operable as the cartridge 10 equipped with the sensor 100 is correctly assembled inside the drug delivery device 1, in particular inside the cartridge holder 30. Then, the electric energy supply 36 is electrically connected to the sensor 100. At least two contact elements 132, 134 provided in or on the housing 4 of the drug delivery device 1 extend through a through opening 39 of the housing 4 and get in direct electrical contact with the contact electrodes 106, 108 on the outer circumference of the cartridge 10 as it is for instance illustrated in FIG. 7. There, the contact element 134 implemented as a contact spring extends through a through opening 39 of the sidewall of the cartridge holder 30 and gets in direct mechanical and electrical contact with the first contact electrode 106.

The further contact element 132 will get in electric contact with the second contact electrode 108 accordingly. Since first and second contact electrodes 106, 108 are separated in axial or longitudinal direction (z) also the radially-inwardly protruding portions of the contact springs of first and second contact elements 132, 134 will be located axially offset with respect to each other. The axial position of the contact elements 132, 134 directly matches and corresponds to the axial position of first and second contact electrodes 106, 108 on the outer circumference of the cartridge 10.

As the contact elements 132, 134 are in electrical contact with the battery 130 the sensor 100 can be supplied with electrical energy upon establishing said electric contact between the contact elements 132, 134 and the respective contact electrodes 106, 108.

The sensor assembly 140 further comprises a processor 110, which in the present embodiment is located in or on the housing 4 of the drug delivery device 1. In addition, the sensor assembly 140 comprises a transceiver 120 that is located and arranged in or on the housing 4 of the drug delivery device 1. In the present embodiment the transceiver 120 is permanently connected to the processor 110 and optionally also to the battery 130 of the electric energy supply 36. It is upon a correct assembly of the cartridge 10 inside the housing 4 that an electrical contact between the measuring electrodes 102, 104 and the processor 110 is established. The processor 110 may be permanently electrically connected to the transceiver and/or to the battery 130.

In any case and since the battery 130 of the electric energy supply 36 is located on or in the housing 4 it is remote from the sensor 100. The design of the sensor 100 can thus be simplified and a low cost sensor can be implemented while offering a large spectrum of functionalities that will be possible with a battery-driven processor 110.

As it is further illustrated in FIG. 5 the electric energy supply 36 comprises a compartment 37 located on the outer circumference of a proximal portion of the cartridge holder 30. The compartment 37 actually accommodates the battery 130, the contact elements 132, 134, the processor 110 and the transceiver 120. The compartment 37 is closable by a closure 38, implemented as a detachable or as a pivotable lid. On a user's request the closure 38 can be opened so as to provide access to the interior of the compartment 37. In this way, an empty battery 130 may be replaced by a new one. Making use of a separate compartment 37 for at least a part of the electric components of the sensor assembly 140 further allows to provide a wired interface on the outer circumference of the housing 4 of the drug delivery device 1.

Instead of a wireless transceiver 120 it is conceivable to provide a standardized wired connector by way of which a wired data transmission may be established to an external electronic device 200. The sensor assembly 140 may be further equipped with an operating element 112 as indicated in FIG. 1, which operating element 112 may be accessible from outside the drug delivery device 1. The operating element 112 may be electrically connectable or may be permanently electrically connected to the processor 110, to the transceiver 120 or to the battery 130. By way of actuating the operating element 112 a measurement process conducted by the processor 110 and/or a data transmitting operable by the transceiver 120 can be triggered. Even though not explicitly shown, the operating element 112 can be also implemented with the drug delivery device 2 and 3 as illustrated in FIGS. 13 to 25.

The transceiver 120 is typically implemented as a wireless transceiver or transponder operable to exchange data and to communicate with an external electronic device 200, such as a mobile phone, a smartphone, a smartwatch, a tablet computer or any other kind of computer or communication system.

The sensor 100 as for instance shown in FIGS. 2 and 3 is typically implemented as a capacitance measuring sensor. For this, the at least first and second measuring electrodes 102, 104 extend almost along the entirety of the longitudinal extension of the flexible foil 101. The electrical capacitance to be measured between these two measuring electrodes 102, 104 when wrapped around the cartridge 10 depends on the axial position of the piston 14 exhibiting an electric susceptibility or permittivity that is distinguishable from the electric susceptibility of the liquid substance 16 located inside the cartridge 10.

The alternative embodiment of a sensor 300 as shown in FIG. 10 is implemented as a temperature sensor. There, the first measuring electrode 102 comprises various heaters 102*a* and the second measuring electrode 104 comprises multiple thermistors 104*a*. As shown in FIG. 10, the various heaters 102*a* and thermistors 104*a* are alternately arranged in longitudinal direction (z) so as to form an alternating array of heaters 102*a* and thermistors 104*a* in longitudinal or axial direction. In this way, the sensor 300 is implemented as a thermal flow sensor. When connected to the electric energy supply 36 the heaters 102*a* may selectively or simultaneously induce a small but distinct heating of a respective portion of the sidewall 12 of the cartridge 10. This change in temperature is detectable by the array of thermistors 104*a*. In this way and due to the different thermal conducting properties of the piston 14 and the liquid substance 16 contained therein the longitudinal position of the piston 14 inside the cartridge 10 could be also determined by way of a temperature measurement. Alternatively and additionally a temperature level the entire cartridge 10 is exposed to can be determined even without making use of a series of heaters 102*a*.

In FIG. 11 another embodiment of attaching the sensor 100 to a cartridge 10 is illustrated. There, and contrary to the embodiment as shown in FIG. 2 the sensor 100 is flipped by 180° so that the first and second contact electrodes 106, 108 are located near a distal end of the cartridge 10. This configuration of sensor 100 and cartridge 10 is particularly provided for the embodiment of the drug delivery device 2 as shown in FIGS. 13-17. In comparison to the embodiment of the drug delivery device 1 as shown in FIG. 5 only a protective cap 50 of the housing 4 as well as the cartridge holder 30 are subject to modification while the residual components, in particular the body 20 of the drug delivery devices 1, 2 are left unchanged.

As it is apparent from a comparison of FIGS. 5 and 13 with the drug delivery device 2 it is the protective cap 60 that is equipped with the electric energy supply 66. As shown in FIG. 13 there is provided a compartment 67 on the outer circumference near a distal end of the protective cap 60. As described already in connection with the electric energy supply 36 of the drug delivery device 1 also with the drug delivery device 2 as shown in FIGS. 13-17 the compartment 37 houses the battery 130 as well as first and second contact elements 132, 134 extending through a through opening 69 of the sidewall of the protective cap 60. The cartridge holder 40 also comprises a window 41 in its sidewall. The window 41 extends in longitudinal direction and almost across the entire longitudinal extension of the tubular-shaped cartridge holder 40.

Also here, the distal end of the cartridge holder 40 comprises a threaded and stepped down socket 42 that serves as an axial abutment for the radially narrowing shoulder portion of the cartridge 10 when assembled inside the cartridge holder 40. As shown in detail in FIGS. 14 and the cartridge holder 40 also comprises a distal through opening 43, through which the pierceable and distal seal 13 of the cartridge 10 is accessible. In the embodiment as shown in FIGS. 13-17 the first and second contact electrodes 106, 108 of the sensor 100 will be accessible through the window 41 of the cartridge holder 40. For this purpose the window 41 is configured as a recess in the sidewall of the cartridge holder 40.

Since the first and second contact electrodes 106, 108 form an almost closed annular structure on the outer circumference of the sidewall 12 of the cartridge 10, the cartridge 10 can be arranged in any arbitrary angular orientation inside the cartridge holder 40 with regard to its longitudinal axis as an axis of rotation. In order to provide a well-defined electric contact between the battery 130, hence between the contact elements 132, 134 and the sensor 100 it is required that the protective cap 60 is arranged in a well-defined orientation onto the cartridge holder 40.

It is of particular benefit, when the cartridge holder 40 and the protective cap 60 are equipped with at least one symmetry-breaking feature as it is for instance shown in the embodiment of the drug delivery device 1 according to FIG. 5. There, the protective cap 50 comprises a recess 51 at its proximal end that serves to receive the radially outwardly protruding compartment 37 located on the outer circumference of a proximal portion of the cartridge holder 30. A similar symmetry-breaking feature is also implemented with the cartridge holder 40 and the protective cap 60 of the drug delivery device 2 as shown in FIGS. 13-17. Apart from that the electric contacting through the through opening 69 between the first and second contact elements 132, 134 is substantially the same as already described in connection with the drug delivery device 1.

By means of the closure 68 the compartment 67 is closeable or sealable. So the interior of the compartment 67 as well as the interior of the protective cap 60 can be effectively protected against environmental influences, such as dust or humidity.

In the further embodiment of a drug delivery device 3 as shown in FIGS. 18-25 substantially the same cartridge holder 40 and the same protective cap 50 as already described in connection with the drug delivery device 1 according to FIGS. 1-9 are provided. Here, at least some of the electronic components of the sensor assembly 140, namely the battery 130, the contact elements 132, 134, the processor 110 and the transceiver 120 are located and arranged in or on an accessory device 70 that is detachably connectable to the outer circumference of the tubular-shaped body 20 of the drug delivery device 3.

The accessory device 70 serves as an electric energy supply 76. It comprises a compartment 77 to house at least the battery 130. In the illustrated embodiments, the compartment 77 also houses the processor 110 and the transceiver 120 as well as the electric contact elements 132, 134. The accessory device 70 comprises a fastening clip 72 that provides a positive engagement of the tubular-shaped body 20 of the drug delivery device 3 with the accessory device 70. In addition to the compartment 77 the accessory device 70 comprises a longitudinal extension 71 extending in distal direction D. The contact elements 132, 134 are located at a distal end of the extension 71.

As it is shown in FIG. 21 the distal end of the accessory device 70 is arrangeable in a radially overlapping way to a proximal portion of the cartridge holder 30. As shown in FIG. 25 the cartridge holder 30 comprises a through opening 39 near its distal end through which the radially inwardly extending contact elements 132, 134 of the accessory device 70 can extend so as to establish an electrical contact with the contact electrodes 106, 108 of the sensor 100 attached to the cartridge 10. The geometric shape of the extension 71 is configured to match with the recess 51 of the protective cap 50. As it is shown in FIGS. 23 and 25 the first and second contact elements 132 are located at a lower side 79 of the extension 71 of the accessory device 70 so as to extend through the through opening 39 of the cartridge holder 30 when the drug delivery device 3 is fully assembled. In this way the contact elements 132, 134 get in electric contact with the first and second contact electrodes 106, 108 of the sensor 100.

Since the extension 71 of the accessory device 70 longitudinally or axially extends across the interface of body 20 and cartridge holder 30 the body 20 can remain completely unchanged compared to a conventional drug delivery device being void of a sensor assembly 140. For the implementation of an electric contact between the sensor 100 located inside the drug delivery device 3 and the accessory device 70 detachably arrangeable on the outer circumference of the body 20 only minor modifications have to be made to the cartridge holder 30. With the accessory device 70 at least some or all electronic components of the sensor assembly 140 can be provided in a separate device, thus leaving the structure of the drug delivery device 3 substantially unchanged. Since the accessory device 70 is detachably connectable to the housing 4 of the drug delivery device 3 it is repeatedly usable with a multiplicity of drug delivery devices 3 that may be implemented as disposable devices.

Rather expensive or spacious electronic components of the sensor assembly 140, such as the battery 130, the transceiver 120 and/or the processor 110 are actually arranged exclusively in the accessory device 70 so that production costs for the sensor 100 as well as required space for said sensor 100 can be effectively reduced to a minimum.

LIST OF REFERENCE NUMBERS 1 drug delivery device
2 drug delivery device
3 drug delivery device
4 housing
5 drive mechanism
10 cartridge
11 barrel
12 sidewall
13 seal
14 piston
15 neck portion
16 liquid substance
20 body
21 dispensing button
22 dose dial
30 cartridge holder
31 window
32 socket
33 through opening
36 electric energy supply
37 compartment
38 closure
39 through opening
40 cartridge holder
41 window
42 socket
43 through opening
50 protective cap
51 recess
60 protective cap
66 electric energy supply
67 compartment
68 closure
69 through opening
70 accessory device
71 extension
72 fastening clip
76 electric energy supply
77 compartment
78 closure
79 lower side
100 sensor
101 flexible foil
101a side
101b side
102 measuring electrode
102a heater
103 longitudinal end section
104 measuring electrode
104a thermistor
105 conductor
106 contact electrode
108 contact electrode
110 processor
112 operating element
120 transceiver
130 battery
132 contact element 134 contact element
140 sensor assembly
200 electronic device

The invention claimed is:

1. A sensor for measuring at least one physical or chemical parameter of a medicament container containing a liquid substance, the sensor comprising:
a planar flexible foil configured to be arranged to an outer circumference of a barrel of the medicament container; and
at least a first and a second measuring electrode arranged and fixed on the planar flexible foil and configured to get in direct mechanical contact with the barrel when arranged to the outer circumference of the barrel;
wherein one of the first and the second measuring electrodes comprises a photo detector.

2. The sensor according to claim 1, wherein the other one of the first and second electrodes comprises a light transmitting device.

3. The sensor according to claim 2, wherein the first and the second measuring electrodes are configured to conduct optical transmission measurements of the barrel.

4. The sensor according to claim 1, wherein the planar flexible foil is dielectric or permeable to dielectric charges.

5. The sensor according to claim 1, wherein the planar flexible foil is transparent.

6. The sensor according to claim 1, wherein the first and the second measurement electrodes are transparent.

7. The sensor according to claim 1, wherein the planar flexible foil is configured to be wrapped around or to be attached to an outer circumference of a sidewall of the barrel.

8. The sensor according to claim 7, wherein the first and the second measuring electrodes are located on an inside-facing portion of the planar flexible foil when the planar flexible foil is wrapped around the outer circumference of the sidewall of the barrel.

9. The sensor according to claim 1, wherein the first and the second measurement electrodes are located on a common side of the planar flexible foil.

10. The sensor according to claim 1, wherein the planar flexible foil is implemented as a label to distinguish the barrel from other identically shaped barrels.

11. The sensor according to claim 1, wherein at least one of the first and the second measuring electrodes comprises a printed or coated conductive structure on or in the planar flexible foil.

12. The sensor according to claim 1, further comprising a first contact electrode and a second contact electrode arranged on the planar flexible foil.

13. The sensor according to claim 12, wherein the first contact electrode is connected to the first measuring electrode and the second contact electrode is connected to the second measuring electrode.

14. The sensor according to claim 12, wherein the first and the second contact electrodes are configured to provide electrical contact to at least one of an electric energy supply, a processor, or a transceiver configured to provide wireless communication with an external electronic device.

15. The sensor according to claim 12, wherein at least one of the first and second contact electrodes forms a ring-shaped contact electrode structure on the outer circumference of the barrel when the planar flexible foil is wrapped around a sidewall of the barrel.

16. The sensor according to claim 12, wherein the first and second contact electrodes extend substantially across an entire lateral dimension of the planar flexible foil.

17. A medicament container comprising a barrel containing a medicament and a sensor wrapped around an outer circumference of a sidewall of the barrel, the sensor comprising:
a planar flexible foil configured to be arranged to an outer circumference of the barrel; and
at least a first and a second measuring electrode arranged and fixed on the planar flexible foil and configured to get in direct mechanical contact with the barrel when arranged to the outer circumference of the barrel;
wherein one of the first and the second measuring electrodes comprises a photo detector.

18. The medicament container according to claim 17, wherein the flexible foil is arranged on the outer circumference of the barrel.

19. The medicament container according to claim 17, wherein the medicament container comprises one of a syringe, a cartridge, a vial, an ampoule, a bottle or a flexible bag.

20. A sensor for measuring at least one physical or chemical parameter of a medicament container containing a liquid substance, the sensor comprising:
a planar flexible foil configured to be arranged to an outer circumference of a barrel of the medicament container; and
at least a first and a second measuring electrode arranged and fixed on the planar flexible foil and configured to get in direct mechanical contact with the barrel when arranged to the outer circumference of the barrel;
wherein one of the first and the second measuring electrodes comprises a light transmitting device.

* * * * *